United States Patent [19]
Brugliera et al.

[11] Patent Number: 5,859,334
[45] Date of Patent: Jan. 12, 1999

[54] GENETIC SEQUENCES ENCODING GLYCOSYLTRANSFERASE ENZYMES AND USES THEREFOR

[75] Inventors: Filippa Brugliera, Preston; Timothy Albert Holton, Northcote, both of Australia

[73] Assignee: International Flower Developments Pty. Ltd., Victoria, Australia

[21] Appl. No.: 379,482

[22] PCT Filed: Jul. 30, 1993

[86] PCT No.: PCT/AU93/00387

§ 371 Date: Mar. 13, 1995

§ 102(e) Date: Mar. 13, 1995

[87] PCT Pub. No.: WO94/03591

PCT Pub. Date: Feb. 17, 1994

[30] Foreign Application Priority Data

Jul. 30, 1992 [AU] Australia ............................ PL3846/92

[51] Int. Cl.$^6$ .............................. A01H 4/00; C12N 15/82; C12N 15/29
[52] U.S. Cl. ................................... 800/205; 800/DIG. 67; 536/23.2; 536/24.3; 435/320.1; 435/172.3
[58] Field of Search ................................. 536/23.2, 24.3; 435/320.1, 172.3; 800/205, DIG. 67

[56] References Cited

U.S. PATENT DOCUMENTS 5,231,020   7/1993   Jorgensen et al. .................... 435/172.3

OTHER PUBLICATIONS

Ralston et al., (1988), "Sequence of Three Bronze Alleles of Maize and Correlation with the Genetic Fine Structure," *Genetics* 119: 185–187.

Furtek et al., (1988), "Sequence Comparisons of Three Wild–Type Bronze–1 Alleles from *Zea mays*," *Plant Molecular Biology* 11: 473–481.

Wise et al., (1990), "Nucleotide Sequence of the Bronze–1 Homologous Gene from *Hordeum vulgare*," *Plant Molecular Biology* 14: 277–279.

Chandler et al., (1989), "Two Regulatory Genes of the Maize Anthocyanin Pathway Are Homologous: Isolation of B Utilizing R Genomic Sequences," *The Plant Cell* 1(12): 1175–1183.

Jonsson et al., (1984), "Properties and Genetic Control of Anthocyanin 5–O–Glucosyltransferase in Flowers of *Petnunia hybrida*," *Planta* 160: 341–347.

Furtek, et al (1988) Plant Molecular Biology 11:473–481.

Ralston, et al. (1988) Genetics 119: 183–197.

Wise, et al (1990) Plant Molecular Biology 14: 277–279.

*Primary Examiner*—Che S. Chereskin
*Attorney, Agent, or Firm*—Scully, Scott, Murphy & Presser

[57] ABSTRACT

The present invention relates generally to genetic sequences encoding flavonoid pathway metabolising enzymes and in particular flavonoid glycosylating enzymes and their use such as in manipulating production of pigmentory molecules in plants. More particularly the present invention provides a genetic sequence encoding UDP rhamnose: anthocyanidin-3-glucoside rhamnosyltransferase (3RT).

35 Claims, 12 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAGAGAGAGA GAGAGAGAGA TCTCGAGTTT TTTTTTTTTT TTTTT    45

( 2 ) INFORMATION FOR SEQ ID NO:2:

( i ) SEQUENCE CHARACTERISTICS:
        ( A ) LENGTH: 1738 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1413

( x i ) SEQUENCE DESCRIPTION: SEQ ID NO:2:

| AAT | GAG | ATG | AAG | CAC | TCA | AAT | GAT | GCA | CTT | CAT | GTG | GTA | ATG | TTC | CCA | 48 |
| --- | --- | --- | --- | --- | --- | --- | --- | --- | --- | --- | --- | --- | --- | --- | --- | --- |
| Asn | Glu | Met | Lys | His | Ser | Asn | Asp | Ala | Leu | His | Val | Val | Met | Phe | Pro | |
| 1 | | | | 5 | | | | | 10 | | | | | 15 | | |
| TTT | TTT | GCT | TTT | GGC | CAT | ATT | AGT | CCA | TTT | GTG | CAG | CTT | GCT | AAC | AAG | 96 |
| Phe | Phe | Ala | Phe | Gly | His | Ile | Ser | Pro | Phe | Val | Gln | Leu | Ala | Asn | Lys | |
| | | | 20 | | | | | 25 | | | | | 30 | | | |
| TTG | TCC | TCT | TAT | GGT | GTC | AAA | GTT | TCT | TTC | TTC | ACA | GCA | TCT | GGC | AAT | 144 |
| Leu | Ser | Ser | Tyr | Gly | Val | Lys | Val | Ser | Phe | Phe | Thr | Ala | Ser | Gly | Asn | |
| | | 35 | | | | | 40 | | | | | 45 | | | | |
| GCC | AGC | AGA | GTC | AAA | TCT | ATG | TTA | AAT | TCT | GCT | CCC | ACT | ACT | CAT | ATA | 192 |
| Ala | Ser | Arg | Val | Lys | Ser | Met | Leu | Asn | Ser | Ala | Pro | Thr | Thr | His | Ile | |
| | 50 | | | | | 55 | | | | | 60 | | | | | |
| GTC | CCT | CTC | ACA | CTT | CCT | CAT | GTT | GAA | GGT | CTA | CCT | CCT | GGT | GCA | GAA | 240 |
| Val | Pro | Leu | Thr | Leu | Pro | His | Val | Glu | Gly | Leu | Pro | Pro | Gly | Ala | Glu | |
| 65 | | | | | 70 | | | | | 75 | | | | | 80 | |
| AGT | ACT | GCA | GAA | TTG | ACA | CCA | GCT | AGT | GCT | GAG | CTT | CTC | AAG | GTT | GCT | 288 |
| Ser | Thr | Ala | Glu | Leu | Thr | Pro | Ala | Ser | Ala | Glu | Leu | Leu | Lys | Val | Ala | |
| | | | | 85 | | | | | 90 | | | | | 95 | | |
| TTA | GAC | CTA | ATG | CAA | CCA | CAA | ATC | AAG | ACT | TTA | CTT | TCC | CAT | CTC | AAA | 336 |
| Leu | Asp | Leu | Met | Gln | Pro | Gln | Ile | Lys | Thr | Leu | Leu | Ser | His | Leu | Lys | |
| | | | 100 | | | | | 105 | | | | | 110 | | | |
| CCC | CAT | TTT | GTT | CTC | TTT | GAT | TTT | GCT | CAA | GAA | TGG | CTT | CCT | AAA | ATG | 384 |
| Pro | His | Phe | Val | Leu | Phe | Asp | Phe | Ala | Gln | Glu | Trp | Leu | Pro | Lys | Met | |
| | | 115 | | | | | 120 | | | | | 125 | | | | |
| GCC | AAT | GGA | TTG | GGT | ATC | AAG | ACT | GTT | TAT | TAC | TCT | GTT | GTT | GTT | GCA | 432 |
| Ala | Asn | Gly | Leu | Gly | Ile | Lys | Thr | Val | Tyr | Tyr | Ser | Val | Val | Val | Ala | |
| | 130 | | | | | 135 | | | | | 140 | | | | | |
| CTT | TCC | ACT | GCT | TTT | CTT | ACT | TGT | CCT | GCT | AGA | GTT | CTT | GAA | CCC | AAA | 480 |
| Leu | Ser | Thr | Ala | Phe | Leu | Thr | Cys | Pro | Ala | Arg | Val | Leu | Glu | Pro | Lys | |
| 145 | | | | | 150 | | | | | 155 | | | | | 160 | |
| AAG | TAT | CCA | AGT | CTC | GAA | GAC | ATG | AAG | AAA | CCT | CCA | CTT | GGG | TTT | CCT | 528 |
| Lys | Tyr | Pro | Ser | Leu | Glu | Asp | Met | Lys | Lys | Pro | Pro | Leu | Gly | Phe | Pro | |
| | | | | 165 | | | | | 170 | | | | | 175 | | |
| CAG | ACC | TCT | GTT | ACC | TCA | GTC | AGA | ACC | TTT | GAG | GCT | AGA | GAT | TTT | CTA | 576 |
| Gln | Thr | Ser | Val | Thr | Ser | Val | Arg | Thr | Phe | Glu | Ala | Arg | Asp | Phe | Leu | |
| | | | 180 | | | | | 185 | | | | | 190 | | | |
| TAT | GTT | TTC | AAG | AGT | TTC | CAT | AAT | GGT | CCT | ACT | TTA | TAT | GAC | CGT | ATA | 624 |
| Tyr | Val | Phe | Lys | Ser | Phe | His | Asn | Gly | Pro | Thr | Leu | Tyr | Asp | Arg | Ile | |
| | | 195 | | | | | 200 | | | | | 205 | | | | |
| CAG | TCA | GGA | CTC | AGG | GGG | TGC | TCA | GCT | ATA | CTA | GCA | AAA | ACT | TGT | TCA | 672 |
| Gln | Ser | Gly | Leu | Arg | Gly | Cys | Ser | Ala | Ile | Leu | Ala | Lys | Thr | Cys | Ser | |
| | 210 | | | | | 215 | | | | | 220 | | | | | |
| CAA | ATG | GAG | GGT | CCT | TAT | ATA | AAA | TAC | GTA | GAA | GCA | CAA | TTC | AAT | AAA | 720 |
| Gln | Met | Glu | Gly | Pro | Tyr | Ile | Lys | Tyr | Val | Glu | Ala | Gln | Phe | Asn | Lys | |
| 225 | | | | | 230 | | | | | 235 | | | | | 240 | |

```
CCT  GTT  TTT  CTA  ATC  GGA  CCC  GTA  GTT  CCG  GAC  CCG  CCT  TCG  GGT  AAA      768
Pro  Val  Phe  Leu  Ile  Gly  Pro  Val  Val  Pro  Asp  Pro  Pro  Ser  Gly  Lys
               245                      250                      255

TTG  GAA  GAG  AAA  TGG  GCT  ACT  TGG  TTA  AAC  AAG  TTT  GAA  GGT  GGA  ACA      816
Leu  Glu  Glu  Lys  Trp  Ala  Thr  Trp  Leu  Asn  Lys  Phe  Glu  Gly  Gly  Thr
               260                      265                      270

GTT  ATT  TAC  TGT  TCT  TTT  GGA  AGT  GAA  ACT  TTC  TTG  ACT  GAT  GAT  CAG      864
Val  Ile  Tyr  Cys  Ser  Phe  Gly  Ser  Glu  Thr  Phe  Leu  Thr  Asp  Asp  Gln
               275                      280                      285

GTC  AAA  GAA  CTG  GCT  TTA  GGT  TTG  GAA  CAG  ACA  GGG  CTT  CCT  TTC  TTT      912
Val  Lys  Glu  Leu  Ala  Leu  Gly  Leu  Glu  Gln  Thr  Gly  Leu  Pro  Phe  Phe
     290                      295                      300

CTT  GTC  TTA  AAT  TTT  CCT  GCA  AAT  GTT  GAT  GTT  TCA  GCG  GAG  CTA  AAC      960
Leu  Val  Leu  Asn  Phe  Pro  Ala  Asn  Val  Asp  Val  Ser  Ala  Glu  Leu  Asn
305                      310                      315                      320

CGA  GCT  TTA  CCT  GAA  GGG  TTT  CTG  GAA  AGA  GTG  AAA  GAC  AAG  GGG  ATT     1008
Arg  Ala  Leu  Pro  Glu  Gly  Phe  Leu  Glu  Arg  Val  Lys  Asp  Lys  Gly  Ile
                    325                      330                      335

ATT  CAT  TCA  GGT  TGG  GTG  CAA  CAG  CAG  CAT  ATA  TTA  GCT  CAT  TCT  AGT     1056
Ile  His  Ser  Gly  Trp  Val  Gln  Gln  Gln  His  Ile  Leu  Ala  His  Ser  Ser
               340                      345                      350

GTA  GGT  TGT  TAT  GTA  TGT  CAT  GCA  GGG  TTT  AGT  TCA  GTT  ATA  GAG  GCA     1104
Val  Gly  Cys  Tyr  Val  Cys  His  Ala  Gly  Phe  Ser  Ser  Val  Ile  Glu  Ala
               355                      360                      365

CTG  GTG  AAT  GAC  TGT  CAA  GTA  GTT  ATG  TTG  CCC  CAG  AAA  GGT  GAC  CAG     1152
Leu  Val  Asn  Asp  Cys  Gln  Val  Val  Met  Leu  Pro  Gln  Lys  Gly  Asp  Gln
     370                      375                      380

ATT  TTG  AAT  GCA  AAG  CTG  GTG  AGT  GGT  GAT  ATG  GAA  GCT  GGG  GTG  GAG     1200
Ile  Leu  Asn  Ala  Lys  Leu  Val  Ser  Gly  Asp  Met  Glu  Ala  Gly  Val  Glu
385                      390                      395                      400

ATT  AAT  AGG  AGG  GAT  GAA  GAT  GGT  TAT  TTT  GGT  AAA  GAA  GAT  ATT  AAG     1248
Ile  Asn  Arg  Arg  Asp  Glu  Asp  Gly  Tyr  Phe  Gly  Lys  Glu  Asp  Ile  Lys
                    405                      410                      415

GAA  GCT  GTG  GAA  AAG  GTG  ATG  GTG  GAT  GTT  GAA  AAG  GAG  CCA  GGT  AAA     1296
Glu  Ala  Val  Glu  Lys  Val  Met  Val  Asp  Val  Glu  Lys  Glu  Pro  Gly  Lys
               420                      425                      430

TTA  ATT  AGG  GAA  AAT  CAG  AAG  AAA  TGG  AAG  GAG  TTT  CTG  TTG  AAC  AAG     1344
Leu  Ile  Arg  Glu  Asn  Gln  Lys  Lys  Trp  Lys  Glu  Phe  Leu  Leu  Asn  Lys
          435                      440                      445

GAT  ATC  CAG  TCC  AAA  TAT  ATT  GGG  AAT  TTA  GTT  AAT  GAA  ATG  ACA  GCC     1392
Asp  Ile  Gln  Ser  Lys  Tyr  Ile  Gly  Asn  Leu  Val  Asn  Glu  Met  Thr  Ala
     450                      455                      460

ATG  GCT  AAG  GTC  TCG  ACT  ACA  TAGGAATCGA  TGTTCCAGC  ATTCTGATGC              1443
Met  Ala  Lys  Val  Ser  Thr  Thr
465                 470

AACAATTTAG  TGTTAAACTA  ATAGACATTA  TGCCTATCCT  TCCAAGCGAG  TTTTTAATT             1503

AAATTTTTGT  GGACAAGTCC  TGAAAGAATG  TGGCTGTAAA  ATGCTACTAT  TTGATTGTCA            1563

GATAAGGTCA  CATTTCATTA  CTTCTCAAGT  TTGTGGCACA  AATCAGCATA  TGATTAAATG            1623

AAGATGGTCT  TTACCAGAAC  ATTTAAATAA  AGGATGAGAT  TCAGTTAAA   AAAAAAAAAA            1683

AAAAAAAAA   AAAAAAAAAA  AAAAAAAAAA  AAAAAAAAAA  AAAAAAAAA   AAAAA                1738
```

( 2 ) INFORMATION FOR SEQ ID NO:3:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
      ( A ) NAME/KEY: CDS
      ( B ) LOCATION: 30..89

( x i ) SEQUENCE DESCRIPTION: SEQ ID NO:3:

```
CTTGCTCGCA GTATTAAACA ACAGGATAT ATG GAG AAT GAG ATG AAG CAC TCA          53
                                Met Glu Asn Glu Met Lys His Ser
                                                475

AAT GAT GCA CTT CAT GTG GTA ATG TTC CCA TTT TTT                          89
Asn Asp Ala Leu His Val Val Met Phe Pro Phe Phe
480                 485                 490
```

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CCCACTGTAA TGTAGCAGTA TT                                                 22
```

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CCAATCCGTC AGATTGGTAT CA                                                 22
```

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
ATGTCTCCTC CAAGTG                                                        16
```

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
CTAGACTCCA ATCAC                                                         15
```

GENETIC SEQUENCES ENCODING GLYCOSYLTRANSFERASE ENZYMES AND USES THEREFOR

The present invention relates generally to genetic sequences encoding flavonoid pathway metabolising enzymes and in particular flavonoid glycosylating enzymes and their use such as in manipulating production of pigmentory molecules in plants.

Bibliographic details of the publications referred to hereinafter in the specification are collected at the end of the description. SEQ ID No's referred to herein in relation to nucleotide and amino acid sequences are defined after the Bibliography.

The flower industry strives to develop new and different varieties of flowering plants. An effective way to create such novel varieties is through the manipulation of flower colour and classical breeding techniques have been used with some success to produce a wide range of colours for most of the commercial varieties of flowers. This approach has been limited, however, by the constraints of a particular species' gene pool and for this reason it is rare for a single species to have a full spectrum of coloured varieties. For example, the development of blue varieties of major cutflower species such as rose, chrysanthemum, tulip, lily, carnation and gerbera would offer a significant opportunity in both the cutflower and ornamental markets.

Flower colour is predominantly due to three types of pigment: flavonoids, carotenoids and betalains. Of the three the flavonoids are the most common and contribute a range of colours from yellow to red to blue. The flavonoid molecules which make the major contribution to flower colour are the anthocyanins which are glycosylated derivatives of cyanidin, delphinidin, petunidin, peonidin, malvidin and pelargonidin, and are localised in the vacuole.

The flavonoid pigments are secondary metabolites of the phenylpropanoid pathway. The biosynthetic pathway for the flavonoid pigments ("flavonoid pathway") is well established. (Ebel and Hahlbrock. 1988; Hahlbrock and Grisebach. 1979: Wiering and De Vlaming, 1984: Schram et al., 1984; Stafford. 1990) and is shown in FIGS. 1A and B. Three reactions and enzymes are involved in the conversion of phenylalanine to p-coumaroyl-CoA, one of the first key substrates in the flavonoid pathway. The enzymes are phenylalanine ammonia-lyase (PAL), cinnamate 4-hydroxylase (C4H) and 4-coumarate: CoA ligase (4CL). The first committed step in the pathway involves the condensation of three molecules of malonyl-CoA (provided by the action of acetyl CoA carboxylase (ACC) on acetyl CoA and $CO_2$), with one molecule of p-coumaroyl-CoA. This reaction is catalysed by the enzyme chalcone synthase (CHS). The product of this reaction, 2', 4,4', 6', tetrahydroxy-chalcone, is normally rapidly isomerized by the enzyme chalcone flavanone isomerase (CHI) to produce naringenin. Naringenin is subsequently hydroxylated at the 3 position of the central ring by flavonol 3-hydroxylase (F3H) to produce dihydrokaempferol (DHK).

The B-ring of dihydrokaempterol can be hydroxylated at either the 3', or both the 3' and 5' positions, to produce dihydroquercetin (DHQ) and dihydromyricetin (DHM), respectively. The pattern of hydroxylation of the B-ring plays a key role in determining petal colour.

The dihydroflavonols (DHK, DHQ and DHM) can also be acted upon by flavonol synthase to produce the flavonois kaempferol, quercetin and myricetin. The flavonols are colourless but act as copigments with the anthocyanins to enhance flower colour.

The next step in the pathway leading to the production of the coloured anthocyanins involves dihydroflavonol-4-reductase (DFR) with the production of the leucoanthocyanidins. These flavonoid molecules are unstable under normal physiological conditions and glycosylation at the 3-position, through the action of glycosyltransferases, stabilizes the anthocyanidin molecule thus allowing accumulation of the anthocyanins. In general, the glycosyltransferases transfer the sugar moieties from UDP sugars and show high specificities for the position of glycosylation and relatively low specificities for the acceptor substrates (Seitz and Hinderer, 1988).

The glycosyltransferases involved in the stabilization of the anthocyanidin molecule include UDP glucose: flavonoid-3-glucosyltransferase (3GT), which transfers a glucose moiety from UDPG to the 3-O-position of the anthocyanidin molecule to produce anthocyanidin-3-glucoside. These anthocyanins can then be glycosylated by another glycosyltransferase, UDP rhamnose: anthocyanidin-3-glucoside rhamnosyltransferase (3RT), which adds a rhamnose group to the 3-O-bound glucose of the anthocyanin molecule to produce the anthocyanidin-3-rutinosides, and once acylated, can be further modified by UDP glucose: anthocyanidin 3-(p-coumraroyl)-rutinoside glucosyltransferase (5GT).

A UDP rhamnose: anthocyanidin-3-glucoside rhamnosyltransferase has been purified from *Silene dioica* (Kamsteeg et al., 1979) and has been shown to use both anthocyanidin-3-glucosides and anthocyanidin-3,5-diglucosides as substrates. The presence of anthocyanidin-3-rutinosides has been reported in Petunia (Stafford, 1990; Jonsson et al., 1982; Maizonnier and Moessner, 1980), Antirrhinum (Martin et al., 1991), cyclamen (Miyajima et al., 1990), Metrosideros (Andersen, 1988), Alstroemeria (Saito et al., 1988), Potentilla spp. (Harborne and Nash, 1984), *Saintpaulia ionantha* (African violet) (Khokhar et al., 1982), Bromeliaceae spp. (Saito and Harborne, 1983), geranium (Asen and Griesbach, 1983) and various other plants. There have been no reports, however, of anthocyanidin-3-rutinosides having been found in rose, although anthocyanidin-3-glucosides and 3,5-diglucosides have been reported. (Asen, 1982). Neither have there been any reports to date of a rhamnosyltransferase cDNA having been isolated from a plant.

In petunia, the UDP rhamnose: anthocyanidin-3-glucoside rhamnosyl-transferase is controlled by the Rt locus on chromosome VI. When both alleles are present in the homozygous recessive state, anthocyanidin-3-glucosides accumulate and further modifications of the anthocyanin molecule such as further glycosylation, acylation and methylation do not occur (Stafford, 1990). The addition of the rhamnose to the anthocyanidin-3-glucosides has a slight blueing effect on the colour (Wiering and de Vlaming, 1984) and a greater spectrum of colours then becomes possible when the anthocyanidin-3-rutinosides are modified by further glycosylation, acylation and methylation.

In addition to the above modifications, pH and copigmentation with other flavonoids such as flavonols and flavones can affect petal colour. Flavonols and flavones can also be glycosylated by glycosyltransferases. The 3-rutinosides of various flavonols have been found in Crocus spp. (Harborne and Williams, 1984), *Lilium cordatum* (Nakano et al., 1989). *Eustoma grandiflorum* (Asen et al., 1986), *Cucurbita pepo* (Itokawa et al., 1981), *Calendula officinalis* (Vidal-Ollivier et al., 1989), *Tulipa gesneriana* (Budzianowski, 1991), Alstoemeria (Saito et al., 1988), Rosa spp. (Asen, 1982), Nicotiana spp. (Snook et al., 1992)

and a number of other plants. The ability to control the activity of 3RT, or other glycosyltransferases such as 5GT, would provide a means of manipulating petal colour thereby enabling a single species to express a broader spectrum of flower colours. Such control may be by modulating the level of production of an indigenous enzyme or by introducing a non-indigenous enzyme.

As used herein an "indigenous" enzyme is one which is native to or naturally expressed in a particular cell. A non-"indigenous" enzyme is an enzyme not native to the cell but expressed through the introduction of genetic material into a plant cell; for example, through a transgene. An "endogenous" enzyme is an enzyme produced by a cell but which may or may not be indigenous to that cell.

In accordance with the present invention, genetic sequences encoding the flavonoid glycosyltransferase enzyme UDP rhamnose: anthocyanidin-3-glucoside rhamnosyltransferase (hereinafter referred to as "3RT"), have been identified and cloned and used to generate transgenic plants. These recombinant sequences permit the further glycosylation of anthocyanidin-3-glucosides such as delphinidin-3-glucoside and cyanidin-3-glucoside, thereby providing a means to manipulate petal colour.

Accordingly, one aspect of the present invention provides an isolated nucleic acid molecule comprising a sequence of nucleotides encoding, or complementary to a sequence encoding a plant flavonoid glycosylating enzyme having the characteristics of a glycosyltransferase or a functional part or derivative of said glycosyltransferase.

More particularly, the present invention is directed to an isolated nucleic acid molecule comprising a sequence of nucleotides encoding or complementary to a sequence encoding a plant glycosyltransferase selected from the group consisting of a flavonoid-5-glucosyltransferase (5GT) and anthocyanidin-3-glucoside rhamnosyltransferase (3RT) or a functional part or derivative of said glycosyltransferase.

The present invention is described and exemplified herein by reference to the identification, cloning and manipulation of genetic sequences encoding 3RT which, up to the present time, is a particularly convenient and useful flavonoid glycosylating enzyme for the practice of the invention herein disclosed. This is done, however, with the understanding that the present invention extends to all novel flavonoid glycosylating enzymes or their functional derivatives. Particularly preferred flavonoid glycosylating enzymes are those which glycosylate, for example, the acylated rutinosides such as delphinidin-3-rutinoside and cyanidin-3-rutinoside but not that which glycosylates the leucoanthocyanidins.

For convenience and by way of short hand notation only, reference herein to a "flavonoid glycosylating enzyme" includes rhamnosyltransferases acting on flavonoids such as anthocyanins, flavonols and/or flavones. Preferably, the flavonoid glycosylating enzyme is 3RT.

A preferred aspect of the present invention, therefore, is directed to an isolated nucleic acid molecule comprising a sequence of nucleotides encoding, or complementary to a sequence encoding 3RT or a functional mutant, derivative, part, fragment, homologue or analogue of 3RT.

By the term "isolated nucleic acid molecule" is meant a genetic sequence in a non-naturally-occurring condition. Generally, this means isolated away from its natural state or formed by procedures not necessarily encountered in its natural environment. More specifically, it includes nucleic acid molecules formed or maintained in vito, including genomic DNA fragments, recombinant or synthetic molecules and nucleic acids in combination with heterologous nucleic acids such as heterologous nucleic acids fused or operably-linked to the genetic sequences of the present invention. The term "isolated nucleic acid molecule" also extends to the genomic DNA or cDNA or part thereof encoding a 3RT or a functional mutant, derivative, part, fragment, homologue or analogue of 3RT in reverse orientation relative to its or another promoter. It further extends to naturally-occurring sequences following at least a partial purification relative to other nucleic acid sequences. The term isolated nucleic acid molecule as used herein is understood to have the same meaning as nucleic acid isolate.

The term "genetic sequence" is used herein in its most general sense and encompasses any contiguous series of nucleotide bases specifying directly, or via a complementary series of bases, a sequence of amino acids comprising a 3RT molecule. Such a sequence of amino acids may constitute a full-length 3RT such as is set forth in SEQ ID No:2 or an active truncated form thereof or a functional mutant, derivative, part, fragment, homologue or analogue thereof or may correspond to a particular region such as an N-terminal, C-terminal or internal portion of the enzyme.

In a preferred embodiment, the sequence of nucleotides substantially corresponds to the nucleotide sequence set forth in SEQ ID No:2 or to a region or part thereof.

According to this preferred aspect of the present invention there is provided an isolated nucleic acid molecule comprising a sequence of nucleotides which:

(i) encodes a 3RT; and (ii) has at least 50% nucleotide sequence similarity to the sequence set forth in SEQ ID No:2.

More particularly, the present invention is directed to an isolated DNA molecule comprising a sequence of nucleotides which:

(i) encodes a 3RT; and (ii) has at least 65–75% nucleotide sequence similarity to the sequence set forth in SEQ ID No:2.

Preferred percentage similarities include 80%, 85%, 90%, 92–95%, 96–98% and 99–100%. Although the pecentage similarities referred to above assume an overall comparison between the sequences set forth in SEQ ID No:2 and another genetic sequence, it is clear that there may be specific regions in the molecules being compared having less than 50% similarity. In this respect, the present invention is further defined as a nucleic acid molecule, and in particular a DNA molecule, comprising a sequence of nucleotides which:

(i) encodes a 3RT; and (ii) has at least 50–75% nucleotide sequence similarity to one or more regions of the sequence set forth in SEQ ID No:2.

In an alternative embodiment, the nucleic acid molecule and more particularly DNA molecule comprises a nucleotide sequence substantially similar to the sequence set forth in SEQ ID No:2 and substantially similar to the sequence set forth in SEQ ID No:3.

The nucleic acid sequences contemplated herein also encompass oligonucleotides useful as genetic probes or as "antisense" molecules capable of regulating expression of the corresponding gene in a plant. An "antisense molecule" as used herein may also encompass a gene construct comprising the structural genomic or cDNA gene or part thereof in reverse orientation relative to its or another promoter.

With respect to this aspect of the invention there is provided an oligonucleotide of 5–50 nucleotides having substantial similarity or complementarity to a part or region of a molecule with a nucleotide sequence set forth in SEQ ID No:2. By "substantial similarity or complementarity" in this context is meant a hybridizable similarity under low, alternatively and preferably medium and alternatively and most preferably high stringency conditions, as defined below. Such an oligonucleotide is useful, for example, in screening 3RT genetic sequences from various sources or for monitoring an introduced genetic sequence in a transgenic plant. The preferred oligonucleotide is directed to a conserved 3RT genetic sequence or a sequence conserved within a plant genus, plant species and/or plant strain or variety.

In one aspect of the present invention, the oligonucleotide corresponds to the 5' or the 3' end of the 3RT genetic sequence. For convenience, the 5' end is considered herein to define a region substantially between the start codon of the structural gene to a centre portion of the gene, and the 3' end is considered herein to define a region substantially between the centre portion of the gene and the terminating codon of the structural gene. It is clear, therefore, that oligonucleotides or probes may hybridize to the 5' end or the 3' end or to a region common to both the 5' and the 3' ends. The present invention extends to all such probes.

In one embodiment, the nucleic acid sequence encoding a 3RT or a functional mutant, derivative, part, fragment, homologue or analogue thereof is used to reduce the activity of an indigenous 3RT, such as by using co-suppression (U.S. Pat. No. 5,034,323). Alternatively, the nucleic acid sequence encoding this enzyme or various functional mutants, derivatives, parts, fragments, homologues or analogues thereof, is used in the antisense orientation to reduce activity of the indigenous 3RT. Although not wishing to limit the present invention to any one theory, it is possible that an antisense 3RT transcript or fragment or part thereof (for example, an oligonuclectide molecule) would form a duplex with all or part of the naturally-occurring mRNA specified for the enzyme thus preventing accumulation of or translation from the mRNA into active enzyme.

In another alternative, ribozymes could be used to inactivate target nucleic acid sequences. Ribozymes are well described by Haseloff and Gerlach (1988). With respect to this embodiment, the ribozyme would preferably comprise a hybridizing portion and a catalytic portion wherein the hybridizing portion comprises one and preferably two nucleotide arms capable of hybridizing to a mRNA transcript from a gene having a nucleotide sequence substantially as set forth in SEQ ID No:2.

Reference herein to the altering of 3RT activity relates to an elevation or reduction in activity of up to 30% or more preferably of 30–50%, or even more preferably 50–75% or still more preferably 75% or greater above or below the normal endogenous or existing levels of activity. Such elevation or reduction may be referred to as "modulation" of 3RT enzyme activity. Generally, modulation is at the level of transcription or translation of 3RT genetic sequences. The level of activity can be assayed using the method of Kamsteeg et al. (1979).

The nucleic acids of the present invention may be ribonucleic acids or deoxyribonucleic acids, single stranded or covalently closed circular molecules. Preferably, the nucleic acid molecule is cDNA. The present invention also extends to other nucleic acid molecules which hybridize to the genetic sequences herein disclosed.

According to this aspect of the present invention there is provided an isolated nucleic acid molecule comprising a sequence of nucleotides which:

(i) encodes a 3RT; and
(ii) hybridizes to the nucleotide sequence set forth in SEQ ID No:2 and/or SEQ ID No:3 or a complementary form thereof under low stringency conditions.

For the purpose of defining the level of stringency, reference can conveniently be made to Maniatis et al. (1982) at pages 387–389, and especially paragraph 11, which is herein incorporated by reference. A low stringency is defined herein as being in 4–6×SSC/1% (w/v) SDS at 37–45° C. for 2–3 hours. Depending on the source and concentration of nucleic acid involved in the hybridization, alternative conditions of stringency may be employed such as medium stringent conditions which are considered herein to be 1–4×SSC/0.5–1% (w/v) SDS at greater than or equal to 45° C. for 2–3 hours or high stringent conditions considered herein to be 0.1–1×SSC/0.1–1.0% SDS at greater than or equal to 60° C. for 1–3 hours.

In its most preferred embodiment, the present invention extends to a nucleic acid molecule having a nucleotide sequence set forth in SEQ ID No:2 or to a molecule having at least 50%, more preferably at least 55%, even more preferably at least 60%, still more preferably at least 65–70%, and yet even more preferably greater than 85% similarity at the level of nucleotide or amino acid sequence to at least one or more regions of the nucleotide or amino acid sequence set forth in SEQ ID No:2 and wherein the nucleic acid encodes or is complementary to a sequence which encodes an enzyme having 3RT activity. It should be noted, however, that nucleotide or amino acid sequences may have similarities below the above given percentages and yet still encode a 3RT-like molecule and such molecules may still be considered within the scope of the present invention where they have regions of sequence conservation.

The nucleic acid molecules contemplated herein may exist in either orientation alone or in combination with a vector molecule and preferably an expression-vector. The term "vector molecule" is used in its broadest sense to include any intermediate vehicle for the nucleic acid molecule, capable of facilitating transfer of the nucleic acid into the plant cell and/or facilitating integration into the plant genome. An intermediate vehicle may, for example, be adapted for use in electroporation, microprojectile bombardment, Agrobacterium-mediated transfer or insertion via DNA or RNA viruses. The intermediate vehicle and/or the nucleic acid molecule contained therein may or may not need to be stably integrated into the plant genome. Such vector molecules may also replicate and/or express in prokaryotic cells. Preferably, the vector molecules or parts thereof are capable of integration into the plant genome. The nucleic acid molecule may additionally contain a promoter sequence capable of directing expression of the nucleic acid molecule in a plant cell. The nucleic acid molecule and promoter may also be introduced into the cell by any number of means such as those described above. The vector molecule may also comprise a genetic sequence encoding a ribozyme as hereinbefore defined capable of cleaving a 3RT mRNA transcript.

The nucleic acid or its complementary form may encode the full-length enzyme or a derivative thereof. By "derivative" is meant any single or multiple amino acid substitutions, deletions, and/or additions relative to the naturally-occurring enzyme and which retains 3RT activity. In this regard, the nucleic acid includes the naturally-occurring nucleotide sequence encoding 3RT or may contain single or multiple nucleotide substitutions, deletions and/or additions to said naturally-occurring sequence. The nucleic acid sequences of the present invention or its complementary form may also encode a "part" of a 3RT, whether active or inactive, and such a nucleic acid molecule may be useful as an oligonucleotide probe, primer for polymerase chain reactions or in various mutagenic techniques, or for the generation of antisense molecules or ribozyme molecules capable of regulating expression of the corresponding gene in a plant.

Amino acid insertional derivatives of the 3RT of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with Table 1, overleaf.

Where 3RT is derivatised by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al. (1989).

Other examples of recombinant or synthetic mutants and derivatives of the 3RT enzyme of the present invention include single or multiple substitutions, deletions and/or additions of any molecule associated with the enzyme such as carbohydrates, lipids and/or proteins or polypeptides.

The terms "analogues" and "derivatives" also extend to any functional chemical equivalent of 3RT and also to any amino acid derivative described above. For convenience, reference to "3RT" herein includes reference to any functional mutant, derivative, part, fragment, homologue or analogue thereof.

TABLE 1

Suitable residues for amino acid substitutions

| Original Residue | Exemplary Substitutions |
| --- | --- |
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |

TABLE 1-continued

Suitable residues for amino acid substitutions

| Original Residue | Exemplary Substitutions |
| --- | --- |
| Phe | Met; Leu; Tyr |
| Ser | Thr |
| Thr | Ser |
| Trp | Tyr |
| Tyr | Trp; Phe |
| Val | Ile; Leu; Met |

The present invention is exemplified using nucleic acid sequences derived from petunia since this represents the most convenient and preferred source of material to date. However, one skilled in the art will immediately appreciate that similar sequences can be isolated from any number of sources such as other plants or certain microorganisms. All such nucleic acid sequences encoding directly or indirectly a 3RT are encompassed by the present invention regardless of their source. Examples of other suitable sources of genes encoding rhamnosyltransferases include, but are not limited to, *Silene dioica,* Antirrhinum, *cyclamen,* Alstroemeria, Metrosideros, Potentilla and *Saintpaulia ionantha.*

In accordance with the present invention, a nucleic acid sequence encoding 3RT may be introduced into and expressed in a transgenic plant in either orientation thereby providing a means either to convert suitable substrates, if synthesized in the plant cell, ultimately into anthocyanidin-3-rutinosides, or alternatively to inhibit such conversion of metabolites by reducing or eliminating endogenous or existing 3RT activity. The production of these anthocyanins will modify petal colour and may contribute to the production of a bluer colour. Expression of the nucleic acid sequence in the plant may be constitutive, inducible or developmental and may also be tissue-specific. The word expression is used in its broadest sense to include production of RNA or of both RNA and protein. It also extends to partial expression of a nucleic acid molecule.

According to this aspect of the present invention there is provided a method for producing a transgenic flowering plant capable of synthesizing 3RT, said method comprising stably transforming a cell of a suitable plant with a nucleic acid sequence which comprises a sequence of nucleotides encoding said 3RT under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous 3RT at elevated levels relative to the amount expressed in a comparable non-transgenic plant.

Another aspect of the present invention contemplates a method for producing a transgenic plant with reduced indigenous or existing 3RT activity, said method comprising stably transforming a cell of a suitable plant with a nucleic acid molecule which comprises a sequence of nucleotides encoding or complementary to a sequence encoding a 3RT activity, regenerating a transgenic plant from the cell and where necessary growing said transgenic plant under conditions sufficient to permit the expression of the nucleic acid.

Yet another aspect of the present invention contemplates a method for producing a genetically modified plant with reduced indigenous or existing 3RT activity, said method comprising altering the Rt gene through modification of the indigenous sequences via homologous recombination from an appropriately altered Rt gene or derivative or part thereof introduced into the plant cell, and regenerating the genetically modified plant from the cell.

In a preferred embodiment, the present invention contemplates a method for producing a transgenic flowering plant exhibiting altered inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence into a 3RT. Alternatively, said method may comprise stably transforming a cell of a suitable plant with a nucleic acid sequence of the present invention or its complementary sequence, regenerating a transgenic plant from the cell and growing said transgenic plant for a time and under conditions sufficient to alter the level of activity of the indigenous or existing 3RT. Preferably the altered level would be less than the indigenous or existing level of 3RT activity in a comparable non-transgenic plant. Without wishing to limit the present invention, one theory of mode of action is that reduction of the indigenous 3RT activity requires the expression of the introduced nucleic acid sequence or its complementary sequence. However, expression of the introduced genetic sequence or its complement may not be required to achieve the desired effect: namely, a flower plant exhibiting altered inflorescence properties.

In a related embodiment, the present invention contemplates a method for producing a flowering plant exhibiting altered inflorescence properties, said method comprising alteration of the Rt gene through modification of the indigenous sequences via homologous recombination from an appropriately altered Rt gene or derivative or part thereof introduced into the plant cell, and regenerating the genetically modified plant from the cell.

Preferably, the altered inflorescence includes the production of different shades of blue or red flowers or other colours, depending on the genotype and physiological conditions of the recipient plant.

Accordingly, the present invention extends to a method for producing a transgenic plant capable of expressing a recombinant gene encoding a 3RT or part thereof or which carries a nucleic acid sequence which is substantially complementary to all or a part of a mRNA molecule optionally transcribable where required to effect regulation of a 3RT, said method comprising stably transforming a cell of a suitable plant with the isolated nucleic acid molecule comprising a sequence of nucleotides encoding, or complementary to a sequence encoding, a 3RT, where necessary under conditions permitting the eventual expression of said isolated nucleic acid molecule, and regenerating a transgenic plant from the cell. By "suitable plant" is meant a plant capable of producing anthocyanidin-3-glucosides and possessing the appropriate physiological properties required for the development of the colour desired.

One skilled in the art will immediately recognise the variations applicable to the methods of the present invention, such as increasing or decreasing the expression of the enzyme naturally present in a target plant leading to differing shades of colours such as different shades of blue or red.

The present invention, therefore, extends to all transgenic plants containing all or part of the nucleic acid sequence of the present invention, or antisense forms thereof and/or any homologues or related forms thereof and in particular those transgenic plants which exhibit altered inflorescence properties. The transgenic plants may contain an introduced nucleic acid molecule comprising a nucleotide sequence encoding or complementary to a sequence encoding a 3RT. Generally the nucleic acid would be stably introduced into the plant genome, although the present invention also extends to the introduction of a 3RT nucleotide sequence within an autonomously-replicating nucleic acid sequence such as a DNA or RNA virus capable of replicating within the plant cell. The invention also extends to seeds from such transgenic plants. Such seeds, especially if coloured, will be useful as proprietary tags for plants.

A further aspect of the present invention is directed to recombinant forms of 3RT. The recombinant forms of the enzyme will provide a source of material for search to develop, for example, more active enzymes and may be useful in developing in vitro systems for production of coloured compounds.

Still a further aspect of the present invention contemplates the use of the genetic sequences described herein in the manufacture of a genetic construct capable of expressing a 3RT or down-regulating an indigenous 3RT enzyme in a plant.

Another aspect of the present invention is directed to a prokaryotic or eukaryotic organism carrying a genetic sequence encoding a 3RT extrachromasomally in plasmid form. In one embodiment the plasmid is pCGP806 in *Escherichia coli*. The microorganism *Escherichia coli* strain XL1-Blue containing the plasmid pCGP806 was deposited with the Australian Government Analytical Laboratories, 1 Suakin Street, Pymble, New South Wales, 2037, Australia on Jul. 29, 1993 and was given Accession Number N93/32139.

The present invention is further described by reference to the following non-limiting Figures and Examples.

In the figures:

FIG. 1 is a schematic representation of the biosynthesis pathway for the flavonoid pigments. Enzymes involved in the first part of the pathway have been indicated as follows: PAL=Phenylalanine ammonia-lyase: C4H=Cinnamate 4-hydroxylase; 4CL=4-coumarate: CoA ligase: CHS= Chalcone synthase; CHI=Chalcone flavanone isomerase; F3H=Flavanone 3-hydroxylase: DFR=Dihydroflavonol-4-reductase (Beld et al., 1989); 3GT=UDP-glucose: flavonoid-3-O-glucosyltransferase; 3RT=UDP rhamnose: anthocyanidin-3-glucoside rhamnosyltransferase and is controlled by the Rt locus. Genetic loci in the latter part of the pathway have been indicated as follows: Gf=the locus that controls acylation; 5-O-glucosylation follows the acylation step but it is not correlated with the Gf locus (Jonsson et al., 1984c); Mt1 and Mt2=loci responsible for 3' methylation (Jonsson et al., 1984b); Mf1 and Mf2=loci responsible for 3', 5' methylation (Jonsson et al., 1984b).

FIG. 2 is a diagrammatic representation of the cDNA insert in the vector pCGN1703 used in the preparation of the petal cDNA library #1.

FIG. 3 is a diagrammatic representation of the plasmid pCGP806. The aE10.9 cDNA insert is indicated as an open box. There is an internal PstI site approximately 100 bp in from the 5' end.

FIG. 4 is a representative autoradiograph from the RFLP analysis of the VR (V/R) $F_2$ plants. Eco RI digested genomic DNA was probed with the aE10.9 cDNA clone. The RFLP designation obtained using the aE10.9 probe partially matched the RFLP designation obtained using the dfr-C probe. V: V23-like RFLP; R: R51-like RFLP; H: heterozygotic(VR) RFLP.

FIG. 5 is a RNA blot analysis of the mRNA encoded by the aE10.9 cDNA in petal limbs from various *P. hybrida* lines. A. Hybridization with $^{32}$P-labelled aE10.9 probe to 20 $\mu$g of total RNA from *P. hybrida* lines. The genotypes of the petunia lines are described in Example 1. Two bands were detected in the R51 line with a longer exposure. B. Hybridization with $^{32}$P-labelled aE10.9 probe to 20 μg of total RNA isolated from pink Tr38 petal limbs with a transposon in the Rt locus (rt*), and from mostly crimson Tr38 petal limbs from which the transposon had excised from one of the Rt alleles (Rt).

Figure 10:
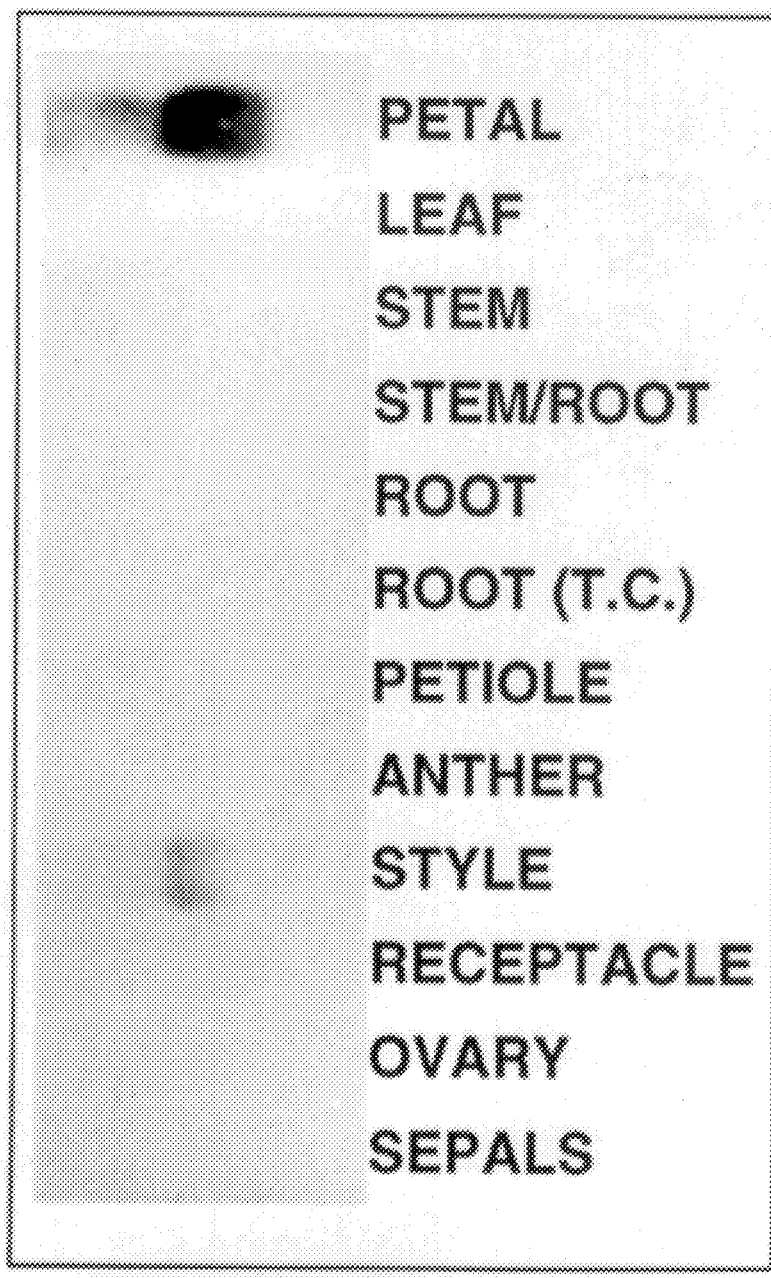

FIG. 10 is a RNA blot analysis of the 3RT mRNA in various parts of the OGB plant. Each lane contained a 20 μg sample of total RNA. All floral parts were from flowers at around stage 3 of development. The vegetative organs were from 6–8 week old seedlings. The stem/root sample is the junction between the stem and root, and the root (T.C.) sample was taken from tissue cultured plantlets.

Figure 11A:
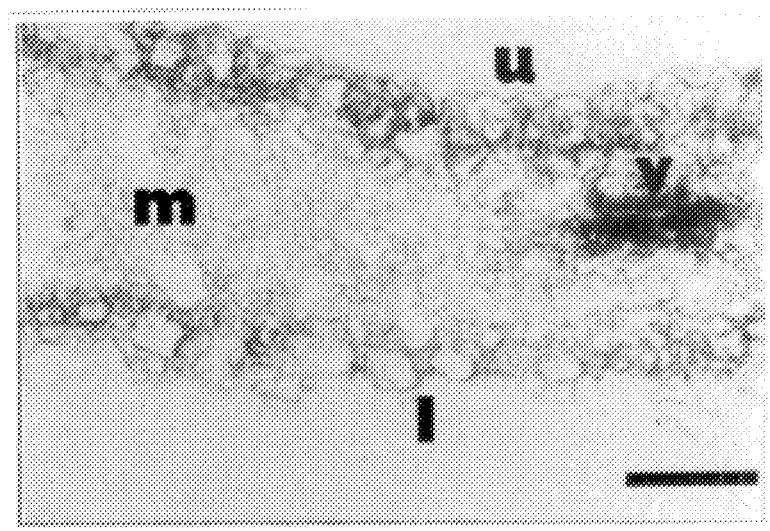
Figure 11B:
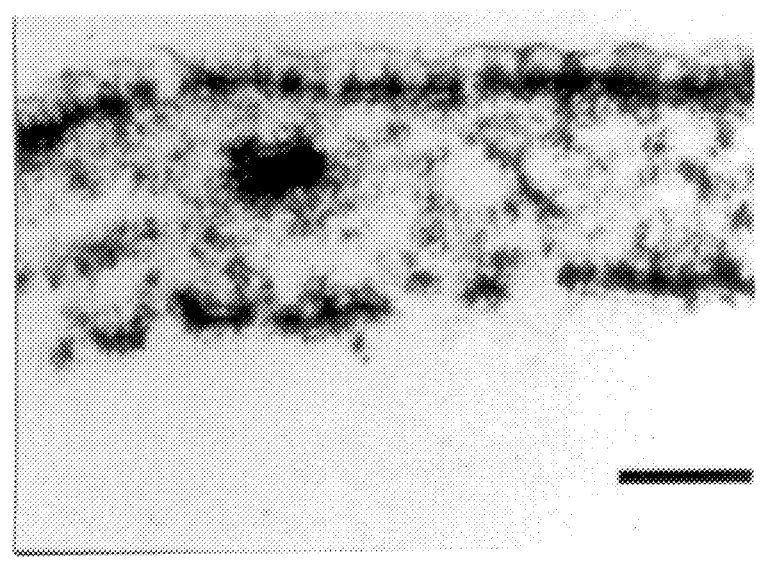

FIG. 11 shows localization of the 3RT RNA in petunia petal buds at stage 3 by in situ hybridization. The plasmid pCGP806 contained the aE10.9 cDNA clone in a pBluescript (Stratagene) vector. The plasmid pCGP806 was linearised with EcoRI so that an antisense RNA transcript could be synthesized using the T7 primer and linearised with XhoI to obtain the sense transcript using the T3 primer. The sense RNA probe was used as a control of non-specific hybridization. A shows the control slide hybridized with the sense aE10.9 transcript. Abbreviations are: u, upper epidermal cell layer; v. vascular bundle; m, mesophyll cells and 1, lower epidermal cell layer. B shows the petal section hybridized with the antisense aE10.9 transcript. Scale bars represent 50 μm.

The amino acid abbreviations used throughout the specification are shown in one following table:

| Amino acid | 3-letter | single-letter |
|---|---|---|
| L-alanine | Ala | A |
| L-arginine | Arg | R |
| L-asparagine | Asn | N |
| L-aspartic acid | Asp | D |
| L-cysteine | Cys | C |
| L-glutamine | Gln | Q |
| L-glutamic acid | Glu | E |
| L-glycine | Gly | G |
| L-histidine | His | H |
| L-isoleucine | Ile | I |
| L-leucine | Leu | L |
| L-lysine | Lys | K |
| L-methionine | Met | M |
| L-phenylalanine | Phe | F |
| L-proline | Pro | P |
| L-serine | Ser | S |
| L-threonine | Thr | T |
| L-tryptophan | Trp | W |
| L-tyrosine | Tyr | Y |
| L-valine | Val | V |

The following is a summary of the SEQ ID No's assigned to nucleotide and amino acid sequences referred to herein:

| Sequence | ID SEQ No |
|---|---|
| Oligo #1 | ID SEQ No: 1 |
| Oligo #2 | ID SEQ No: 6 |
| Oligo #3 | ID SEQ No: 7 |
| Oligo #4 | ID SEQ No: 4 |
| Oligo #5 | ID SEQ No: 5 |
| aE10.9 | ID SEQ No: 2 |
| aE10.12 | ID SEQ No: 3 |

EXAMPLE 1

PLANT MATERIAL

The *Petunia hybrida* varieties used are presented in Table 2.

TABLE 2

| Plant variety | Properties | Source/Reference |
|---|---|---|
| Old Glory Blue (OGB) | F$_1$ Hybrid | Ball Seed, USA |
| V23 | An1, An2, An3, An4, An6, An8, An9, An10, ph1, Hf1, Hf2, ht1, Rt, po, B1, F1 | Wallroth et al. (1986) Doodeman et al. (1984) |
| R51 | An1, An2, An3, an4, An6, An8, An9, An10, An11, Ph1, hf1, hf2, Ht1, rt, Po, b1, f1 | Wallroth et al. (1986) Doodeman et al. (1984) |
| Skr4 | An1, An2, An3, An4, An6, An11, hf1, hf2, Ph1, Ph2, Ph5, rt, Po, Mf1, Mf2, f1 | I.N.R.A., Dijon, Cedex France |
| VR | V23 × R51 F$_1$ Hybrid | |
| R18 | An1, An2, An3, An4, An6, An8, An9, An10, An11, hf1, hf2, Ph1, Ph2, Ph3, Ph5, rt, f1, Ht1 | I.N.R.A., Dijon, Cedex France |
| Sd5 | An1, An2, An3, An4, An6, An9, An10, An11, hf1, Hf2, Ph1, Ph2, Ph5, rt, f1, ht1, ht2, mf2, Gf, po | I.N.R.A., Dijon, Cedex France |
| Dla51 | An1, an2, An3, an4, An6, An9, An10, An11, Hf1, Ph1, Ph2, Ph5, rt, f1, Ht1, mf1, mf2, Mt1, Gf, po | I.N.R.A., Dijon, Cedex France |
| Da | An1, An2, An3, an4, An6, An9, An10, An11, Hf1, Hf2, Ph1, Ph2, Ph5, rt, f1, Ht1, mf1, mf2, Mt1, Gf, po | I.N.R.A., Dijon, Cedex France |
| SD | Skr4 × Da F1 hybrid | |
| Tb1-3 | An1, An2, An3, an4, An6, An9, An10, An11, Hf1, Hf2, Ph1, Ph2, Ph5, Rt, f1, Ht1, mf1, mf2, Mt1, Gf, po | I.N.R.A., Dijon, Cedex France |
| Ba20 | an1, An2, an4, An6, hf1, hf2, Ph1, Ph2, Ph5, Rt, f1, Ht1, mf1, mf2, Gf, po | I.N.R.A., Dijon, Cedex France |
| Tr38 | An1, An2, an4, An6, Hf1, Ph1, Ph2, Ph5, rt-38inst., f1, Ht1, mf1, mf2, Mt1, Gf, po | I.N.R.A., Dijon, Cedex France |

Plants were grown in specialized growth rooms with a 14 hr day length at a light intensity of 10,000 lux and a temperature of 22° to 26° C. OGB flowers were harvested at developmental stages defined as follows:

Stage 1: Unpigmented, closed bud (<25 mm in length).

Stage 2: Pigmented, closed bud (25–35 mm in length).

Stage 3: Dark purple bud with emerging corolla (>35 mm in length).

Stage 4: Dark purple opened flower pre-anther dehiscence (>50 mm in length).

Stage 5: Fully opened flower with all anthers dehisced.

Flowers of the other varieties were harvested prior to anther dehiscence at the stage of maximum pigment accumulation.

EXAMPLE 2

BACTERIAL STRAINS

The *Escherichia coli* strains used were:

| | |
|---|---|
| DH5α | supE44, Δ(lacZYA-ArgF)U169, (φ80lacZΔM15), hsdR17)$r_k^-$, $m_k^+$), recA1, endA1, gyrA96, thi-1, relA1, deoR. (Hanahan, 1983 and BRL, 1986). |
| XL1-Blue | supE44, hsdR17($r_k^-$, $m_k^+$), recA1, endA1, gyrA96, thi-1, relA1, lac⁻, [F'proAB, lacI$^q$, lacZΔM15, Tn10(tet$^R$)] (Bullock et al., 1987). |
| PLK-F | recA, hsdR17($r_k^-$, $m_k^+$), mcrA⁻, mcrB⁻, lac⁻, supE44, galK2, galT22, metB1, [F'proAB, lacI$^q$, lacZΔM15, Tn10(tet$^R$)] Stratagene). |

The disarmed *Agrobacterium tumefaciens* strain used was AGL0 (Lazo et al., 1991).

The cloning vectors pBluescript and pBluescribe were obtained from Stratagene.

E. coli transformation

Transformation of the *E. coli* strains was performed according to the method of Inoue et al., (1990).

EXAMPLE 3

GENERAL METHODS

Synthesis of Oligonucleotides

Oligonucleotides were synthesized on an Applied Biosystems PCR-Mate DNA synthesizer using methods recommended by the manufacturer. The oligonucleotides synthesized were, 5'-3':

| | | |
|---|---|---|
| Oligo #1 | GAGAGAGAGAGAGAGAGAGATCTCGAGTTTTTTTTTTTTTTTTTT | SEQ ID No: 1 |
| Oligo #2 | ATGTCTCCTCCAGTG | SEQ ID No: 6 |
| Oligo #3 | CTAGACTCCAATCAC | SEQ ID No: 7 |
| Oligo #4 | CCCACTGTAATGTAGCAGTATT | SEQ ID No: 4 |
| Oligo #5 | CCATACCGTCAGATTGGTATCA | SEQ ID No: 5 |

Preparation of $^{32}$P-labelled cDNA probes

Twenty micrograms of total RNA was incubated at 100° C. for 2 minutes and then cooled on ice for a further 2 minutes. The RNA was added to a reaction mixture containing 20 μg/ml oligo-dT, 50 mM Tris-HCl pH 8.0. 75 mM KCl, 30 mM MgCl$_2$, 10 mM DTT, 0.5 mg/mL actinomycin D, 200 μM dATP. 200 μM dGTP, 200 μM dTTP, 2.5 μM dCTP, 100 μCi [α-$^{32}$P]-dCTP (Bresatec, 3000 Ci/mmol), 40 units RNasin (Promega), and 600 units Moloney Murine Leukaemia Virus reverse transcriptase (BRL) and incubated for 1 hour at 37° C. EDTA and NaOH were added to a final concentration of 50 mM and 0.2M, respectively and the mixture was incubated for 20 minutes at 70° C. The mixture was then neutralised by addition of HCl to a concentration of 0.2M. Unincorporated [α-$^{32}$P]-dCTP was removed by chromatography on a Sephadex G-50 (Fine) column.

$^{32}$P-Labelling of DNA Probes

DNA fragments (50 to 100 ng) were radioactively labelled with 50 μCi of [α-$^{32}$P]-dCTP using an oligolabelling kit (Bresatec). Unincorporated [α-$^{32}$P]-dCTP was removed by chromatography on a Sephadex G-50 (Fine) column.

EXAMPLE 4

Construction of cDNA library #1

Total RNA was isolated from the petal tissue of *P. hybrida* cv OGB stage 3 to 4 flowers using the method of Turpen and Griffith (1986). Poly(A)$^+$ RNA was selected from the total RNA by three cycles of oligo-dT cellulose chromatography (Aviv and Leder, 1972).

Figure 2:
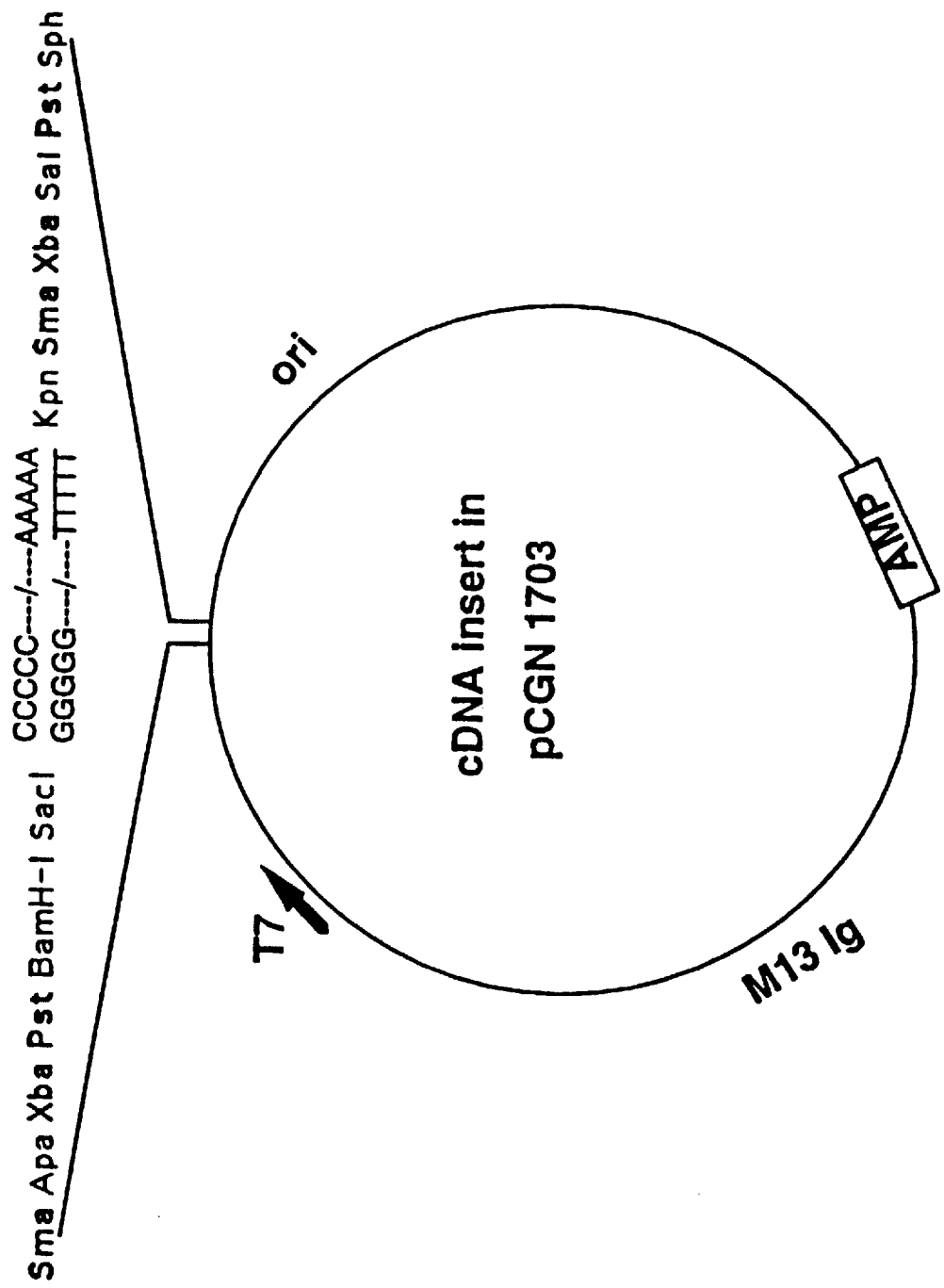

Four micrograms of mRNA prepared from the five developmental stages of *P. hybrida* cv OGB were used to construct a cDNA library using the dimer-primer method (Alexander et al., 1984) in pCGN1703 (FIG. 2). Plasmid pCGN1703 is a plasmid vector based on pBluescribe M13– (Stratagene) and was constructed by Calgene Inc. (California, U.S.A.). The polylinker sites were changed so that the cDNA insert is flanked by PstI, XbaI and SmaI sites. A HinDIII/PvuII fragment which included the T3 primer and the lac promoter was deleted.

The library was plated at a high density onto LB (Sambrook et al., 1989)+ampicillin (100 μg/mL) plates and incubated at 37° C. for 16 hours. Colonies were then scraped off and suspended in LB broth+15% (v/v) glycerol and stored at −70° C. Twenty thousand colonies of the amplified library were plated onto LB+ampicillin (100 μg/mL) plates at a density of 2,000 colonies per plate and incubated at 32° C. for 16 hours. After incubation at 4° C. for 1 hour, duplicate colony lifts were taken onto Colony/Plaque Screen™ filters (DuPont) and treated as recommended by the manufacturer.

Differential Screening of cDNA library#1

A differential screening approach was used to isolate cDNA clones coding for genes expressed in OGB petal (stages 3–4) but reduced or absent in R51 petals (stages 3–4). Twenty thousand colonies were screened at 2,000 colonies per 15 cm plate. Prior to hybridization the filters were prewashed in a solution of 50 mM Tris-HCl pH 8.0, 1M NaCl, 1 mM EDTA, 0.1% (w/v) sarcosine (prewashing solution) at 42° C. for 30 minutes. They were then rinsed in 2×SSC, 1% (w/v) SDS. Duplicate colony lifts were prehybridized (42° C., 1 hr) and hybridized (42° C. 16 hrs) in 50% (v/v) deionised formamide, 1M NaCl, 1% (w/v) SDS, 10% dextran sulphate (w/v) (hybridization solution). Degraded salmon sperm DNA (100 μg/mL) and poly U (20 μg/mL) were added with the $^{32}$P-labelled cDNA probes (3×10$^6$ cpm/mL) prior to the hybridization step. The filters were washed in 2×SSC, 1% (w/v) SDS at 65° C. for 2×60 minutes followed by 0.2×SSC, 1% (w/v) SDS at 65° C. for 30 minutes and exposed to Kodak XAR film with an intensifying screen at −70° C. for 16 hours.

From the above differential screen 196 cDNA clones were isolated and placed into ordered arrays. These arrays were then probed with cDNA probes prepared from total RNA extracted from OGB petals (stages 3–4), OGB petals (stage 5) and OGB leaves. Seventy-eight out of the 196 cDNA clones were preferentially expressed in the OGB petals (stages 3–4) compared to the OGB petals (stage 5) and to the OGB leaves. These were selected for sibling analysis, RNA blot analysis and sequence analysis.

EXAMPLE 5

SIBLING ANALYSIS
Isolation and Purification of cDNA Inserts

In order to determine which of the 78 cDNA clones were siblings, labelled cDNA inserts from a selection were hybridized to the ordered arrays. cDNA inserts were isolated from the plasmid vector by restricting with the appropriate restriction endonucleases and electrophoresing in low melting agarose gel in a TAE running buffer. The correct DNA fragment was then cut out and purified by three phenol: chloroform: isoamyl alcohol (50:49:1) extractions followed by two ether extractions and an ethanol precipitation. The DNA pellet was finally resuspended in TE (10 mM Tris-HCl, 1 mM EDTA pH 7.5) and an estimation of the concentration was made by electrophoresing an aliquot on an agarose gel alongside a known amount of SPP-1 DNA restricted with EcoRI (Bresatec).

Positive cDNA clones were picked off the plates into LB+ampicillin (100 µg/mL) broth and grown at 37° C. for 16 hours. Aliquots of the overnight cultures (200 µ) were then placed into microtitre trays to form ordered arrays. In order to screen these cDNA clones the arrays were replicaplated onto Colony/Plaque Screen™ filters (DuPont) that had been laid on top of LB+ampicillin (100 µg/mL) plates. The bacteria were grown at 28° C. for 16 hours, followed by a 2 hour incubation at 37° C. The filters were removed and treated by floating on a solution of 10% (w/v) SDS for 2 minutes followed by air drying on a layer of blotting paper. The DNA was baked onto the filters using the autoclave method (Allday and Jones, 1987). Prior to hybridization the filters were washed in prewashing solution at 42° C. for 30 minutes and rinsed in 2×SSC, 1% (w/v) SDS. Prehybridization and hybridization steps were carried out as previously described.

Thirteen cDNA clones cross-hybridized to a cDNA clone (aE10) under high stringency conditions. The clone with the longest cDNA insert (0.9 kg) was designated pCGP711 and a clone with a shorter cDNA insert (0.5 kg) was designated pCGP712.

EXAMPLE 6

ISOLATION OF A LONGER cDNA CLONE

The aE10 cDNA clone isolated from cDNA library #1 was only 0.9 kg in length. In order to isolate a full length cDNA, 16.000 pfu from cDNA library #2 were screened with the cDNA insert from pCGP711.

Construction of cDNA library #2

Two micrograms of poly(A)$^+$ RNA were reverse transcribed in a 20 µL volume containing 1×Superscript™ reaction buffer, 10 mM dithiothreitol, 500 µM dATP. 500 µM dGTP, 500 µM dTTP. 500 µM 5-methyl-dCTP, 0.75 µg oligonucleotide #1 (SEQ-ID No.1) and 2 µL Superscript™ reverse transcriptase (BRL). The reaction mix was incubated at 37° C. for 50 minutes, 44° C. for 10 minutes, then placed on ice.

Second strand reaction mix (140 µL) was added to the first strand reaction. The second strand reaction mix consisted of 21 mM Tris-HCl, 104 mM KCl, 5.3 mM MgCl$_2$, 171 µM β-NAD, 11.4 mM (NH$_4$)$_2$SO$_4$, 214 µM dATP, 642 µM dCTP, 214 µM dGTP, 214 µM dTTP, 4 mM DTT, 10 µCi $^{32}$P-dCTP (3000 Ci/mMole), 15 units E. coli DNA ligase, 40 units E. coli DNA polymerase I (Boehringer) and 0.8 units RNAse H. The final mixture was incubated for 150 minutes at 16° C. To make the double-stranded cDNA blunt-ended, 10 units T4 DNA polymerase was added, and the reaction continued for a further 15 minutes at 16° C. The reaction was stopped and the cDNA purified by phenol/chloroform extraction, followed by chloroform extraction and ethanol precipitation.

EcoRI adaptors (Promega) were ligated with the cDNA and then kinased using conditions recommended by the manufacturer. The enzymes were denatured by heat (70° C., 20 minutes) and the DNA was purified by phenol/chloroform extraction and ethanol precipitation. The cDNA was digested with 50 units XhoI (Boehringer) in a reaction volume of 100 µL, using conditions recommended by the manufacturer. The enzyme was heat killed (70° C. 20 minutes) and the mixture passed through an S400 spun column (Pharmacia) which had been equilibrated in STE buffer (Sambrook et al., 1989). The eluate was phenol/chloroform extracted and ethanol precipitated. After microcentrifugation at 4° C. for 30 minutes the cDNA pellet was rinsed with 70% (v/v) ethanol, air dried and resuspended in 10 µL of TE buffer (1 mM Tris-HCl (pH7.5), 1 mM EDTA).

A 2.5 µL aliquot of the cDNA mixture was ligated with 1 g λZAPII EcoRI/XhoI/CIAP treated vector (Stratagene) in 5 µL reaction buffer consisting of 50 mM Tris-HCl (pH 7.0), 10 mM MgCl$_2$, 10 mM dithiothreitol, 1 mM ATP and 2 units T4 DNA ligase. The reaction was performed at 4° C. for 4 days.

After incubating at room temperature for two hours, the ligation reaction mixture was packaged using the Packagene system (Promega). The total number of recombinants was 1×10$^6$ pfu.

After transfecting PLK-Fcells, the packaged cDNA was plated at 50,000 pfu per 15 cm diameter plate. The plates were incubated at 37° C. for eight hours, and the phage were eluted in 100 mM NaCl, 8 mM MgSO$_4$, 50 mM Tris-HCl pH 8.0, 0.01% gelatin (Phage Storage Buffer (PSB)). Chloroform was added and the phage stored at 4° C. as an amplified library.

Plasmid Isolation

Helper phage R408 (Stratagene) was used to excise pBluescript phagemids containing petunia cDNA inserts from the amplified λZAP cDNA library #2 using methods described by the manufacturer. E. coli XL1-Blue were transfected with the phagemid mixture and the colonies were plated out on LB plates (Sambrook et al., 1989) containing 100 µg/mL ampicillin. Single colonies were analysed for cDNA inserts by rowing in LB broth (Sambrook et al., 1989)+ampicillin (100 µg/mL) and isolating the plasmid using the alkali-lysis procedure (Sambrook et al., 1989). Once the presence of a cDNA insert had been determined larger amounts of plasmid DNA were prepared from 5 mL overnight cultures using the alkali-lysis procedure. Plasmid DNA was further purified by banding on a CsCl gradient (Sambrook et al., 1989).

Screening of cDNA library #2

Prior to hybridization the duplicate plaque lifts were washed in prewashing solution at 42° C. for 30 minutes; stripped in 0.4M sodium hydroxide at 42° C. for 30 minutes; then washed in a solution of 0.2M Tris-HCl pH 8.0. 0.1× SSC. 0.1% (w/v) SDS at 42° C. for 30 minutes and finally rinsed in 2×SSC, 1.0% (w/v) SDS. Prehybridization was carried out at 42° C. for 1 hr; $^{32}$P-labelled probe (1×10$^5$ cpm/mL) was then added to the hybridization solution and hybridization continued at 42° C. for a further 16 hrs.

The filters were then washed in 2×SSC, 1% (w/v) SDS at 65° C. for 2×30 minutes followed by 0.2×SSC, 1% (w/v)

SDS at 65° C. for 30 minutes and exposed to Kodak XAR film with an intensifying screen at −70° C. for 16 hours.

Figure 3:
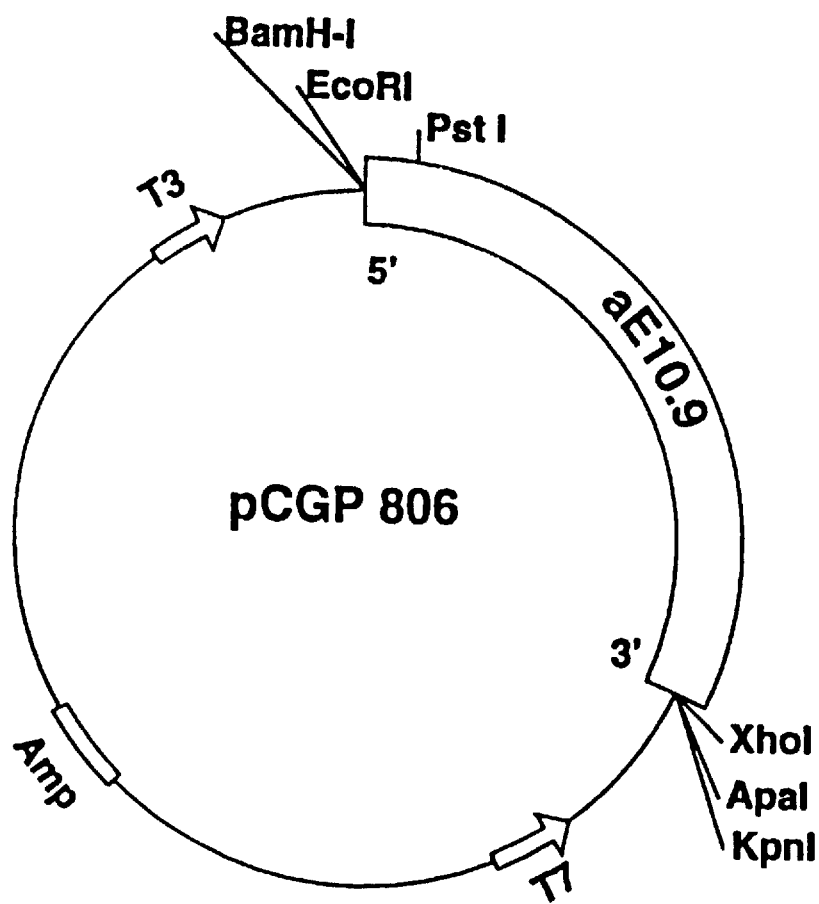
Figure 4:
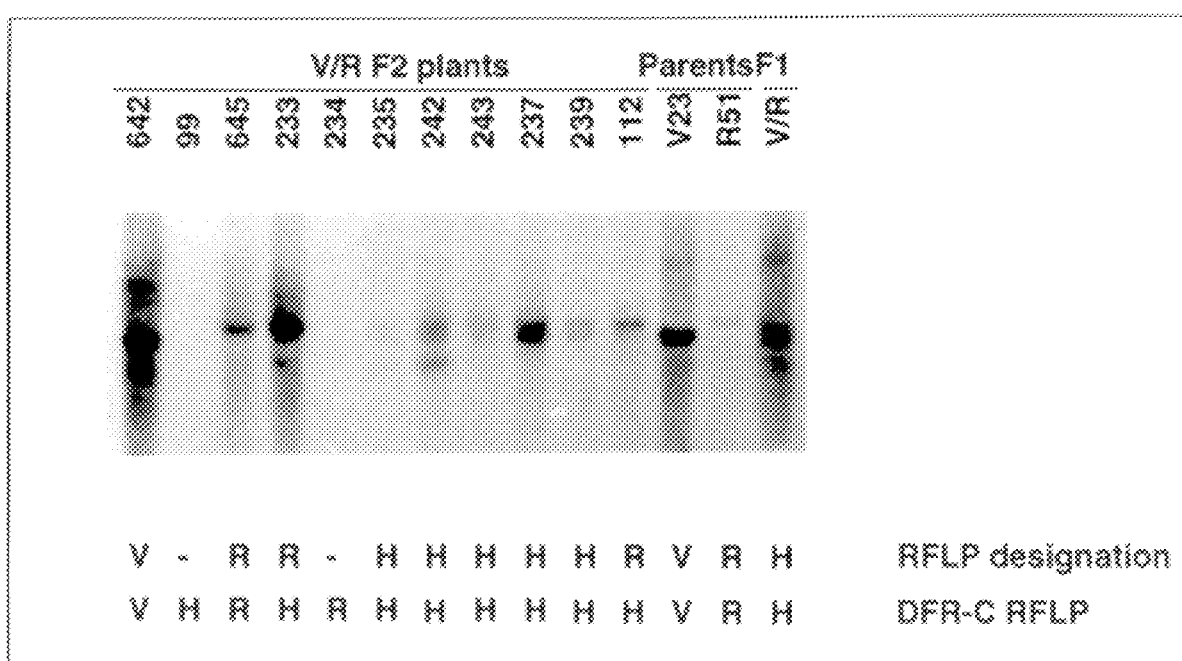

One of 13 hybridizing clones, designated pCGP806 contained a cDNA insert (aE10.9) of 1.7 kb and was chosen for further analysis (FIG. 3). Another of the 13 hybridizing clones designated pCGP820 was subsequently shown to contain a slightly longer cDNA insert (aE10.12).

EXAMPLE 7

DNA SEQUENCE ANALYSIS

DNA sequencing was performed essentially by the method of Sanger et al. (1977), using the Sequenase enzyme (USB. version 2.1). The complete sequence of aE10.9 was determined using the Erase-a-base kit (Promega) (SEQ ID No:2). Partial sequence of the pCGP820 cDNA clone (aE10.12) is shown in SEQ ID No:3.

Homology searches against Genbank, SWISS-PROT and EMBL databases were performed using the FASTA and TFASTA programs (Pearson and Lipman, 1988).

The complete sequence of aE10.9 is shown in SEQ ID No:2. It contained an open reading frame of 1407 bases from the first methionine which encodes a polypeptide of 469 amino acids. The open reading frame continues upstream from the first methionine as is shown from the partial sequence of the 5' end of the cDNA insert from pCGP820 (SEQ ID No:3) that shows another in-phase methionine occurs 4 amino acids upstream from the first aE10.9 methionine. The amino acid sequence encoded by aE10.9 showed similarity to both the maize Bz1 UDP glucose:flavonol-3-O-glucosyltransferase (Furtek et al., 1988: Ralston et al., 1988) and the *Hordeum vulgare* 3GT (Wise et al., 1990) (Tables 3A and 3B). The region of most similarity (36%) spanned 130 amino acids from amino acid 262 to 396 of the aE10.9 cDNA sequence. The latter half of this region from amino acid 335 to 387 (spanning 52 amino acids) also showed homology (around 32%) to other glycosyltransferases from non-plant sources: namely, glucuronosyltransferases from human (Ritter et al., 1991), mouse (Kimura and Owens, 1987) and rat (Mackenzie, 1986) and an ecdysteroid glucosyltransferase from *Autograpia californica* nuclear polyhedrosis virus (O'Reilly and Miller, 1989, 1990). A comparison of the amino acid sequence of the glycosyltransferases from the plant, human and viral sources over the 52 amino acid span, is shown in Table 4. The sequence alignments were performed using the Clustal program (Higgins and Sharp 1988).

TABLE 3A

Comparison of the aE10.9 deduced amino acid sequence from 1–313, with other plant glycosyltransferases. Region of homology of the deduced aE10.9 amino acid sequence to 3GT from *H. vulgare* (GT-BARLEY) and 3GT from *Z. mays* (Bz1-MAIZE). The conserved amino acids are in bold and are indicated by asterisks under the sequence and conservative substitutions are indicated by dots under the sequence.

| Name | Amino acid sequence | Amino acid No. |
|---|---|---|
| aE10.9: | ------MKHSNDALHVVMFPFF--AFGHISPFVQLANKLSSYGVKVSFF-TASGNASRVK | 51 |
| Bz1-MAIZE[1]: | MAPADGESSPPPHVAVVAFPFSSHAAVLLSIARALAAAAAPSGATLSFLSTASSLAQLRK | 60 |
| GT-BARLEY[2]: | MAP------PPPHIAVVAFPFSSHAAVLFSFARAL-AAAAPAGTSLSFLTTADNAAQLRK | 53 |
|  | . ** *** * * * * .** ** * * |  |
| aE10.9: | SM-------LNSAPTTHIVPLTLPHVEGLPPGAESTAELTPASAELLKVALDLMQPQIKT | 104 |
| Bz1-MAIZE: | ASSASAGHGLPGNLRFVEVPDGAPAAEET-VPVPRQMQLFMEAAEAGGVKAWLEAARAAA | 119 |
| GT-BARLEY: | AGA------LPGNLRFVEVPDGVPPGETACLSPPRRMDLFMAAAEAGGVRVGLEAACASA | 107 |
|  | * ** * * . * ** * * |  |
| aE10.9: | LLSHLKPHFVLFDFAQEWLPKMANGLGIKTVYYSVVVALSTAFL----TCPAR------- | 153 |
| Bz1-MAIZE: | GGARVTC--VVGDAFVWPAADAAASAGAPWVP--VWTAASCALLAHIRTDALREDVGDQA | 175 |
| GT-BARLEY: | GGARVSC--VVGDAFVWT-ADAASAAGAPWVA--VWTAASCALLAHLRTDALRRDVGDQA | 162 |
|  | . . *. * * * * * * *.* * * |  |
| aE10.9: | ------VLEPKKYPSLEDMKKPPLGFPQTSVTSVRTFEARDFLYVFKSFHNGPTLYDRIQ | 207 |
| Bz1-MAIZE: | ANRVDGLLISHPGLASYRVRDLPDG-----------VVSGDFNYVINLL-----VHRMGQ | 219 |
| GT-BARLEY: | ASRADELLVAHAGLGGYRVRDLPDG-----------VVSGDFNYVISLL-----VHRQAQ | 206 |
|  | . * .. * * ** ** . . * |  |
| aE10.9: | SGLRGCSAILAKTCSQMEGPYIKYVEAQFNKPVFLIGPVV--------------PDPPSG | 253 |
| Bz1-MAIZE: | CLPRSAAAVALNTFPGLDPPDVTAALAEILPNCVPFGPYHLLL-AEDDADTA-APADPHG | 277 |
| GT-BARLEY: | RLPKAATAVALNTFPGLDPPDLIAALAAELPNCLPLGPYHLLPGAEPTADTNEAPADPHG | 266 |
|  | . *. * .. * . * ** * * * |  |
| aE10.9: | KLEEKWATWLNKFEGGTVIYCSFGSETFLTDDQVKELALGLEQTGLPFFLVLNFPANVDV | 313 |
| Bz1-MAIZE: | CLA-----WLGRQPARGVAYVSFGTVACPRPDELRELAAGLEDSGAPFLWSLREDSWPHL | 332 |
| GT-BARLEY: | CLA-----WLDRRPARSVAYVSFGTNATARPDELQELAAGLEASGAPFLWSLRGVVAAA- | 320 |
|  | * * * . * * * *** * .. *** *** * ** * |  |

TABLE 3B

Comparison of the aE10.9 deduced amino acid sequence from 314–469, with other plant glycosyltransferases. Region of homology of the deduced aE10.9 amino acid sequence to 3GT from *H. vulgare* (GT-BARLEY) and 3GT from *Z. mays* (Bz1-MAIZE). The conserved amino acids are in bold and are indicated by asterisks under the sequence and conservative substitutions are indicated by dots under the sequence.

| Name | Amino acid sequence | Amino acid No. |
|---|---|---|
| aE10.9: | SAELNRALPEGFLERVKDKGI-IHSGWVQQQHILAHSSVGCYVCHAGFSSVIEALVNDCQ | 372 |
| Bz1-MAIZE[1]: | --------PPGFLDRAAGTGSGLVVPWAPQVAVLRHPSVGAFVTHAGWASVLEGLSSGVP | 384 |
| GT-BARLEY[2]: | --------PRGFLERAP----GLVVPWAPQVGVLRHAAVGAFVTHAGWASVMEGVSSGVP | 368 |
|  | * *** *       *   *  * **  * ***   **  * . | |
| aE10.9: | VVMLPQKGDQILNAKLVSGDMEAGVEINRRDEDGYFGKEDIKEAVEKVMVDVEKEPGKLI | 432 |
| Bz1-MAIZE: | MACRPFFGDQRMNARSVAHVWGFGAA--------FEGAMTSAGVATAVEELLRGEEGARM | 436 |
| GT-BARLEY: | MACRPFFGDQTMNARSVASVWGFGTA--------FDGPMTRGAVANAVATLLRGEDGERM | 420 |
|  |   * *** **. *        *            * .  * * . | |
| aE10.9: | R----ENQKKWKEFLLNKDIQSKYIGNLVNEMTAMAKVSTT | 469 |
| Bz1-MAIZE: | RARAKELQALVAEAFGPGGECRKNFDRFVEIVCRA------ | 471 |
| GT-BARLEY: | RAKAQELQAMVGKAFEPDGGCRKNFDEFVEIVCRV------ | 455 |
|  | *    * *        *     . * . | |

[1]Furtek et al., Ralston et al., 1988
[2]Wise et al., 1990

TABLE 4

The area of amino acid sequence similarity of aE10.9 compared to various glycosyltransferases including the plant glucosyltransferases described in Table 3, a viral ecdysteroid glucosyltransferase (GT-ECD) and a human glucuronosyltransferase (GT-HUMAN). Amino acid positions are indicated by the numbers preceding the sequence.

| Name | Amino acid No. | Amino acid sequence |
|---|---|---|
| aE10.9: | 335 | IHSGWVQQQHILAHSSVGCYVCHAGFSSVIEALVNDCQVVMLPQKGDQILNA |
| Bz1-MAIZE[1]: | 347 | LVVPWAPQVAVLRHPSVGAFVTHAGWASVLEGLSSGVPMACRPFFGDQRMNA |
| GT-BARLEY[2]: | 331 | LVVPWAPQVGVLRHAAVGAFVTHAGWASVMEGVSSGVPMACRPFFGDQTMNA |
| GT-ECD[3]: | 345 | ITQNWFNQRAVLRHKKMAAFITQGGLQSSDEALEAGIPMVCLPMMGDQFYHA |
| GT-HUMAN[4]: | 350 | ILVKWWPQNDLLGHPMTRAFITHaGSHGVYESICNGVPMVMMRLFGDQMDNA |
|  |  | .   *   * .* *       ... *     *  .         *** . * |

[1]Furtek et al., 1988; Ralston et al., 1991
[2]Wise et al., 1990
[3]O'Reilly and Miller, 1989, 1990
[4]Ritter et al., 1991

EXAMPLE 8

RFLP Analysis

Isolation of Genomic DNA

DNA was isolated from leaf tissue essentially as described by Dellaporta et al., (1983). The DNA preparations were further purified by CsCl buoyant density centrifugation (Sambrook et al, 1989).

Southern blots

The genomic DNA (10 μg) was digested for 16 hours with 60 units of EcoRI and electrophoresed through a 0.7% (w/v) agarose gel in a running buffer of TAE (40 mM Tris-acetate, 50 mM EDTA). The DNA was then denatured in denaturing solution (1.5M NaCl/0.5M NaOH) for 1 to 1.5 hours, neutralized in 0.5M Tris-HCl (pH 7.5)/1.5M NaCl for 2 to 3 hours and then transferred to a Hybond N (Amersham) filter in 20×SSC.

Isolation of DFR-C probe

A fragment of the dfr-C gene was amplified by PCR using V23 genomic DNA as template and two oligonucleotide primers, #4 (SEQ ID No:4) and #5 (SEQ ID No:5) obtained from the published dfr-C sequence (Gerats et al., 1990). The resulting 170 bp PCR product was gel purified and isolated onto NA-45 membrane (Schleicher and Schuell). After elution the PCR product was ligated into the ddT-tailed pBluescript M13⁻ vector (Stratagene) described by Holton and Graham (1991) and sequenced to confirm that the cloned fragment corresponded to the published sequence.

RFLP analysis

Southern blots of V23 and R51 genomic DNA probed with aE10.9 revealed one hybridizing band in both lines under high stringency conditions. RFLP analysis was used to investigate linkage of the gene corresponding to the aE10.9 cDNA to known genetic loci. Analysis of EcoRI digested genomic DNA isolated from a V23×R51 $F_2$ population revealed a RFLP for the aE10.9 probe which was linked to dfc-C. Dfr-C is a molecular marker for chromosome VI and is linked to Rt (Beld et al., 1989). There was co-segregation of the aE10.9 and dfr-C RFLPs for 26 out of 34 V23×R51 $F_2$ plants. This represents a recombination frequency of 8.1% which is similar to a reported recombination frequency of 13% between B and dfr-C (Cornu et al., 1990).

EXAMPLE 9

NORTHERN ANALYSIS

Total RNA was isolated from tissue that had been frozen in liquid $N_2$ and ground to a fine powder using a mortar and pestle. An extraction buffer of 4M guanidium isothiocyanate, 50 mM Tris-HCl (pH 8.0), 20 mM EDTA, 0.1% (v/v) Sarkosyl, was added to the tissue and the mixture was homogenized for 1 minute using a polytron at maximum speed. The suspension was filtered through Miracloth (Calbiochem) and centrifuged in a JA20 rotor for 10 minutes at 10.000 rpm. The supernatant was collected and made to 0.2 g/mL CsCl (w/v). Samples were then layered over a 10 mL cushion of 5.7M CsCl, 50 mM EDTA (pH 7.0) in 38.5 mL Quick-seal centrifuge tubes (Beckman) and centrifuged at 42.000 rpm for 12–16 hours at 23° C. in a Ti-70 rotor. Pellets were resuspended in TE/SDS (10 mM Tris-HCl (pH 7.5), 1 mM EDTA, 0.1% (w/v) SDS) and extracted with phenol:chloroform:isoamyl alcohol (25:24:1) saturated in 10 mM EDTA (pH 7.5). Following ethanol precipitation the RNA pellets were resuspended in TE/SDS.

RNA samples were electrophoresed through 2.2M formaldehyde/1.2% (w/v) agarose gels using running buffer containing 40 mM morpholinopropanesulphonic acid (pH 7.0), 5 mM sodium acetate, 0.1 mM EDTA (pH 8.0). The RNA was transferred to Hybond-N filters (Amersham) as described by the manufacturer and probed with $^{32}$p-labelled cDNA fragment ($10^8$ cpm/µg, $2\times10^6$ cpm/mL). Prehybridization (1 hr at 42° C.) and hybridization (16 hr at 42° C.) were carried out in 50% (v/v) formamide, 1M NaCl. 1% (w/v) SDS, 10% (w/v) dextran sulphate. Degraded salmon sperm DNA (100 µg/mL) was added with the $^{32}$P-labelled probe for the hybridization step.

Filters were washed in 2×SSC, 1% (w/v) SDS at 65° C. for 1 to 2 hours and then 0.2×SSC, 1% (w/v) SDS at 65° C. for 0.5 to 1 hour. Filters were exposed to Kodak XAR film with an intensifying screen at −70° C. for 16 hours.

Expression in mutants

Figures 5A, 5B:
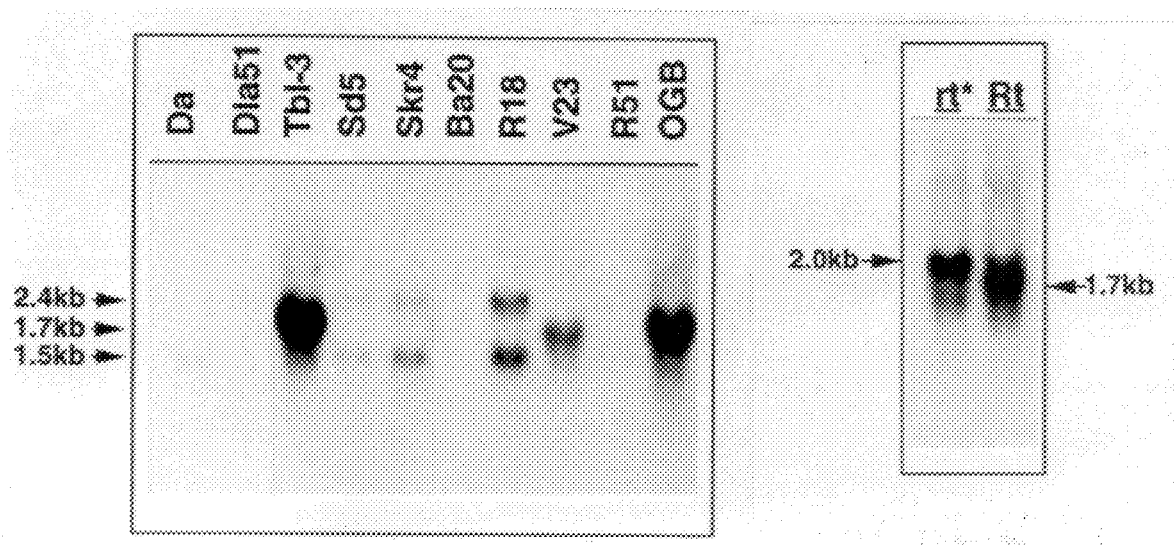

The influence of three genetic loci (Rt, An1 and An2) on accumulation of the mRNA hybridizing to the aE10.9 probe was examined (FIG. 5A). As described earlier Rt controls rhamnosylation of anthocyanidin-3-glucosides while An1 and An2 are regulatory genes which control the activity of a number of structural genes involved in anthocyanin biosynthesis (Gerats et al., 1984). In the petal tissue of Rt/Rt, An1/An1, An2/An2 lines (Da, Sd5, Skr4, R18 and R51) two mRNAs of about 2.4 kb and 1.5 kb were detected with the aE10.9 probe compared to only one mRNA of about 1.7 kb in OGB and other Rt/Rt, An1/An1, An2/An2 (Tbl-3 and V23) lines. The R51, V23 and OGB lines were also probed with the shorter aE10.9 cDNA sibling clones (data not shown). The 0.5 kb cDNA insert of pCGP712 which began at nucleotide 736 of the aE10.9 sequence (SEQ ID No:2) only detected the 2.4 kb transcript in the R51 line. The 0.9 kb cDNA insert of pCGP711 which began at nucleotide 1217 of the aE10.9 sequence (SEQ ID No:2), detected both the 2.4 and 1.5 kb transcripts in the R51 line. Both of the 0.5 kb and 0.9 kb cDNA clones detected the wild-type transcript in the V23 and OGB lines. There was no detectable expression of mRNA hybridizing to the aE10.9 probe in the An1/An1 or An2/An2 lines (Ba20, Dla51, Pla3 and Tlh1).

The Rt locus in the petunia line Tr38 is unstable due to the presence of a transposon (Cornu, 1977). Revertant crimson petals develop when the transposon has excised at an early stage of flower development. Total RNA isolated from pink petals of Tr38 (rt*) and from crimson reverted petals of Tr38 (Rt) was examined for expression of mRNA hybridizing to the aE10.9 probe (FIG. 5B). The aE10.9 probe detected a 2.0 kb RNA species in the rt* petal tissue and a 1.7 kb transcript in the revertant tissue.

EXAMPLE 10

PREPARATION OF CONSTRUCTS

Construction of pCGP293

The expression binary vector pCGP293 was derived from the Ti binary vector pCGN1559 (McBride and Summerfelt, 1990). Plasmid pCGN1559 was digested with KpnI and the overhanging 3' ends were removed with T4 DNA polymerase according to standard protocols (Sambrook et al., 1989). The vector was then further digested with XbaI and the resulting 5' overhang was repaired using the Klenow fragment of DNA polymerase I. The vector was then re-ligated to give pCGP67. A 1.97 kb PstI fragment containing the Mac promoter, mas terminator and various cloning sites (Comai et al., 1990) was isolated from pCGP40 and inserted into the PstI site of pCGP67 to give pCGP293.

Plasmid pCGP40 was constructed by removing the GUS gene (Jefferson et al. 1987) as a BamHI-SacI fragment from pCGN7334 and replacing it with the BamHI-SacI fragment from pBluescribe M13⁻ that includes the multicloning site. Plasmid pCGN7334, obtained from Calgene Inc. (California, U.S.A.), was constructed by inserting the fragment containing the Mac-GUS-mas gene fusion into the XhoI site of pCGN7329 (Comai et al., 1990).

Construction of pCGP810

Plasmid pCGP810 was constructed by cloning the cDNA insert from pCGP806 in a sense orientation behind the Mac promoter (Comai et al., 1990) of pCGP293. The plasmid pCGP806 was restricted with BamHI and KpnI to release the cDNA insert. The cDNA fragment was isolated on a low melting agarose gel and ligated with BamHI/KpnI ends of the pCGP293 binary vector. The ligation was carried out using the Amersham ligation kit with 400 ng of the pCGP293 binary vector and 85 ng of the 1.7 kb aE10.9 cDNA fragment. Correct insertion of the insert in pCGP810 was established by PstI restriction analysis of DNA isolated from gentamycin resistant transformants.

Construction of pCGP811

Figure 7:
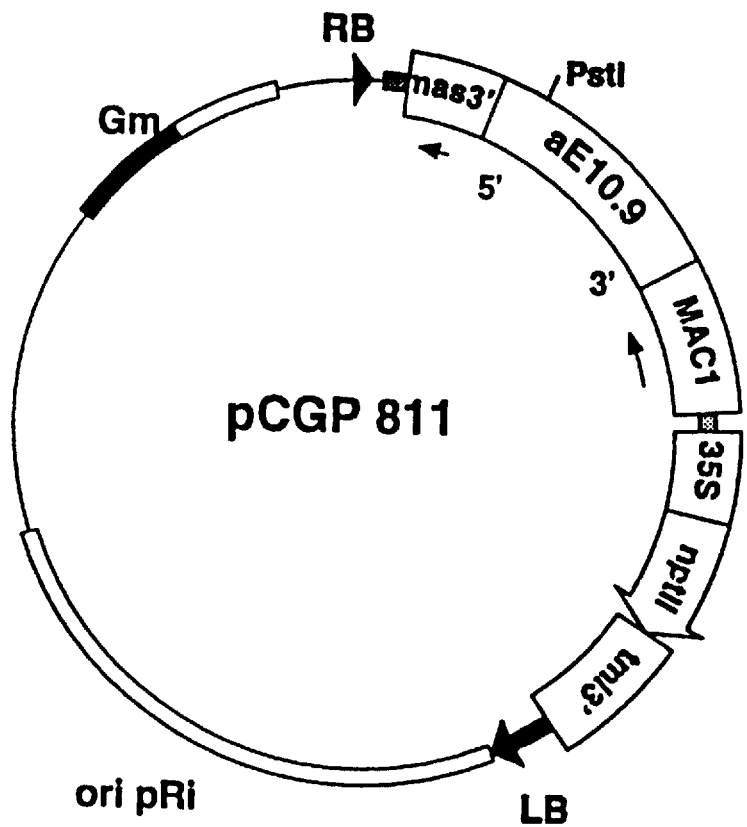
FIG. 7 is a diagrammatic representation of the binary plasmid pCGP811. The cDNA insert from pCGP806 was cloned in an antisense orientation behind the Mac promoter of the expression vector pCGP293, as illustrated.

Plasmid pCGP811 (FIG. 7) was constructed by cloning the cDNA insert from pCGP806 in an antisense orientation behind the Mac promoter (Comai et al., 1990) of pCGP293. Plasmid pCGP806 was firstly restricted with ApaI. The overhanging 3' ends were "chewed back" with DNA polymerase (Klenow fragment) as described in Sambrook et al., 1989. The plasmid was then restricted with XbaI to isolates the fragment containing the cDNA insert. The XbaI 5' overhanging ends were filled in using DNA polymerase (Klenow fragment) (Sambrook et al., 1989). The cDNA fragment was isolated on a low melting agarose gel and ligated with flushed XbaI/BamHI ends of the pCGP293 binary vector. The ligation was carried out using the Amersham ligation kit with 400 ng of the pCGP293 binary vector and 85 ng of the 1.7 kb aE10.9 cDNA fragment. Correct insertion of the insert in pCGP811 was established by PstI restriction analysis of DNA isolated from gentamycin resistant transformants.

EXAMPLE 11

A. TUMEFACIENS TRANSFORMATIONS

Figure 6:
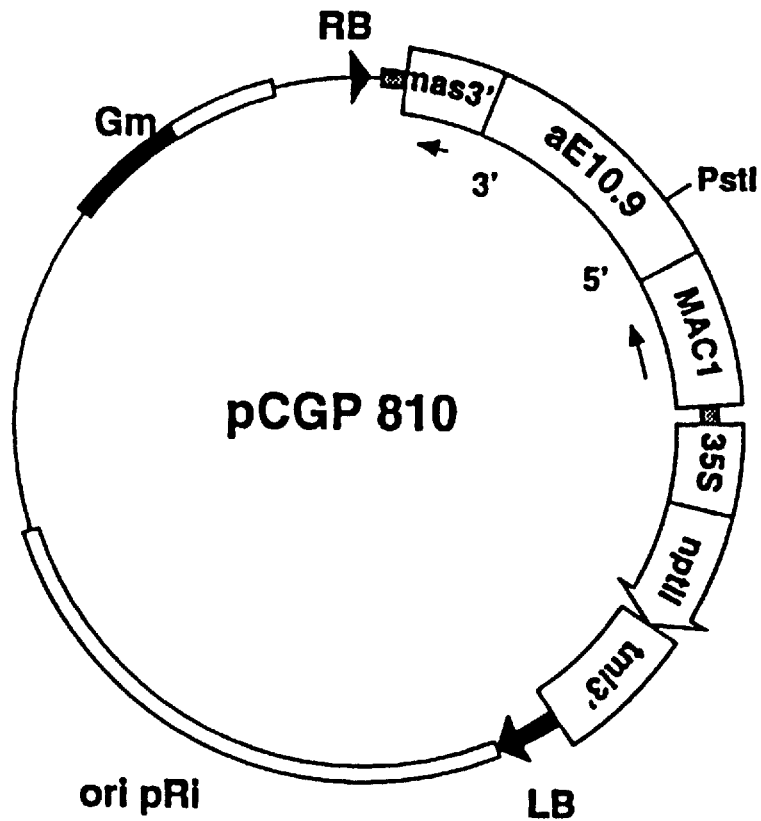
FIG. 6 is a diagrammatic representation of the binary plasmid pCGP810. The cDNA insert from pCGP806 was cloned in a sense orientation behind the Mac promoter of the expression vector pCGP293. as illustrated.

The plasmids pCGP811 and pCGP810 (FIGS. 6 and 7) were introduced into the Agrobacterium tumefaciens strain AGL0 by adding 5 µof each plasmid DNA to 100 µL of competent AGL0 cells prepared by inoculating a 50 mL MG/L (Garfinkel and Nester, 1980) culture and growing for 16 hrs with shaking at 28° C. The cell were then pelleted and resuspended in 0.5 mL of 85% (v/v) 100 mM $CaCl_2$/15% (v/v) glycerol. The DNA-Agrobacterium mixture was frozen by incubation in liquid $N_2$ for 2 minutes and then allowed to thaw by incubation at 37° C. for 5 minutes. The DNA/bacterial mix was then placed on ice for a further 10 minutes. The cells were then mixed with 1 mL of MG/L media and incubated with shaking for 16 hours at 28° C. Cells of A. tumefaciens carrying pCGP811 or pCGP810 were selected on MG/L agar plates containing 100 µg/mL gentamycin. The presence of pCGP811 or pCGP810 was confirmed by Southern analysis of DNA isolated from the gentamycin resistant transformants.

EXAMPLE 12

PETUNIA TRANSFORMATIONS

Plant Material

Leaf tissue from mature plants of P. hybrida cv VR was sterilized in 1.25% (v/v) sodium hypochlorite for 2 minutes and then rinsed three times in sterile water. The leaf tissue was then cut into 25 mm² squares and precultured on MS media (Murashige and Skoog, 1962) supplemented with 0.05 mg/L kinetin and 1.0 mg/L 2,4dichlorophenoxyacetic acid (2,4-D) for 24 hours.

Co-cultivation of Agrobacterium and Petunia Tissue

A. tumefaciens strain AGLO (Lazo et al., 199 1) containing the binary vector pCGP811 or pCGP810 (FIG. 6 & 10) was maintained at 4° C. on MG/L (Garfinkel and Nester, 1980) agar plates with 100 mg/L gentamycin. A single colony was grown overnight in liquid medium containing 1% (w/v) Bacto-peptone, 0.5% (w/v) Bacto-yeast extract and 1% (w/v) NaCl. A final concentration of $5 \times 10^8$ cells/mL was prepared the next day by dilution in liquid MS medium containing B5 vitamins (Gamborg et al., 1968) and 3% (w/v) sucrose (BPM). The leaf discs were dipped for 2 minutes into BPM containing AGL0/pCGP811 or AGL0/pCGP810 as described above. The leaf discs were then blotted dry and placed on co-cultivation media for 4 days. The co-cultivation medium consisted of SH medium (Schenk and Hildebrandt, 1972) supplemented with 0.05 mg/L kinetin and 1.0 mg/L 2,4-D and included a feeder layer of tobacco cell suspension spread over the co-cultivation medium with a filter paper placed on top of the tobacco cell suspension.

Recovery of transgenic petunia plants

After co-cultivation, the leaf discs were transferred to MS medium supplemented with 3% (w/v) sucrose, α-benzylaminopurine (BAP) (1 mg/L for VR leaf discs or 4.0 mg/L for SD leaf discs), 0.1 mg/L α-naphthalene acetic acid (NAA), kanamycin (300 mg/L for VR leaf discs or 100 mg/L for SD leaf discs), 350 mg/L cefotaxime and 0.3% (w/v) Gelrite Gellan Gum (Schweizerhall) (selection medium). Regenerating explants were transferred to fresh selection medium after 4 weeks. Adventitious shoots which survived the kanamycin selection were isolated and transferred to BPM containing 100 mg/L kanamycin and 200 mg/L cefotaxime for root induction. All cultures were maintained under a 16 hr photoperiod (60 µmol. m-2, s-1 cool white fluorescent light) at 23°±2° C. When roots reached 2–3 cm in length the transgenic petunia plantlets were transferred to autoclaved Debco 51410/2 potting mix in 8 cm tubes. After 4 weeks plants were replanted into 15 cm pots using the same potting mix and maintained at 23° C. under a 14 hour photoperiod (300 µmol, m-2, s-1 mercury halide light).

EXAMPLE 13

TRANSGENIC PLANT PHENOTYPE ANALYSIS
pCGP810 in SD

Table 5 shows the various petal and pollen colour phenotypes obtained with SD plants transformed with the pCGP810 plasmid. Both of the transgenic plants #2129 and #2128 produced flowers with altered petal and pollen colour as well as flowers, that resembled the control SD. That changes in pollen colour were observed on introduction of plasmid pCGP 810 into SD petunia plants was an unanticipated outcome. The codes are taken from the Royal Horticultural Society's Colour Chart. They provide an alternative means by which to describe the colour phenotypes observed. The designated numbers, however, should be taken only as a guide to the perceived colours and should not be regarded as limiting the possible colours which may be obtained.

TABLE 5

| ACCESSION NUMBER | RHSCC CODE | PETAL COLOUR | POLLEN COLOUR |
|---|---|---|---|
| VR | 80A | purple | blue |
| SD control | 63B/C | dark pink | white/green |
| 2128 | 63B/C | SD like | white/green |
| 2129 | 64C | variegated pink/purple | blue |
| 2130 | 71B/C | purple | blue |

RHSCC = Royal Horticultural Society Colour Chart.

pCGP811 in VR

Table 6, overleaf, shows the various colour phenotypes obtained with VR plants transformed with the pCGP811 plasmid. The codes are again taken from the Royal Horticultural Society's Colour Chart, and as stated above, should be taken only as a guide to the perceived colours and not regarded as limiting the possible colour which may be obtained.

TABLE 6

| ACCESSION NUMBER | RHSCC CODE | PETAL COLOUR |
|---|---|---|
| VR control | 80A | purple |
| 2127 | 80A | VR like |
| 2123 | 64B, 67A, 71C | dark pink |
| 2125 | 71D | dark pink |
| 2126 | 67C + 78A | variegated pink/purple |
| 2122 | 71C | dark pink |
| 2132 | 80A | VR like |
| 2129 | 64B | red/pink |
| 2124 | 80A | VR like |
| 2130 | 80A | VR like |
| 2128 | 74B | dark pink |
| 2144 | 80A | VR like |
| 2131 | 67C + 78A | variegated pink/purple |

RHSCC = Royal Horticultural Society Colour Chart.

EXAMPLE 14

EXTRACTION OF PIGMENTS

Anthocyanidins

Prior to HPLC or TLC analysis the anthocyanin molecules present in petal extracts acid hydrolysed to remove glycosyl moieties from the anthocyanidin core. The hydroxylation pattern on the B ring of the anthocyanidin pigments was determined by HPLC or TLC analysis of the anthocyanidin core molecule.

Flower pigments were extracted and hydrolysed by incubating a petal limb with 1 mL of 2M hydrochloric acid at 100° C. for thirty minutes. The hydrolysed anthocyanins were extracted with 200 µL of iso-amylalcohol. This mixture was then dried down vacuum and resuspended in a smaller volume of 20 µL iso-amylalcohol. A 5 µL aliquot of the extracts from the pCGP810 in SD petals, anthers and styles was spotted onto a TLC plate. An aliquot (5 µL) of the extracts from the pCGP811 in VR petals was removed and dried down under vacuum and resuspended in 200 µL of 50% (v/v) acetonitrile and 0.5% (v/v) TFA.

Anthocyanins

Non-hydrolysed pigment extracts of the transgenic petunia flowers were prepared by adding the petal limbs, styles or anthers to 1 mL of methanol/1% (v/v) HCl and incubating in the dark at 4° C. for 16 hours. The extracts were then removed and dried down under vacuum. The pigments were resuspended in 100 μL of methanol/1% (v/v) HCl. An aliquot of the extracts from the pCGP811 in VR petals and from the pCGP810 in SD petals was spotted onto a TLC plate.

HPLC analysis of anthocyanidins

A 5 μL aliquot of the anthocyanidins from the pCGP811 in VR petals in 200 μL of 50% (v/v) acetonitrile and 0.5% (v/v) TFA was analysed by HPLC via gradient elution using gradient conditions of 50% B to 60% B over 10 minutes, then 60% B for 10 minutes and finally 60% B to 100% B over 5 minutes where solvent A consisted of TFA: $H_2O$ (5:995) and solvent B consisted of acetonitrile: TFA: $H_2O$ (500:5:495). An Asahi Pac ODP-50 cartridge column (250 mm ×4.6 mm ID) was used for the reversed phase chromatographic separations. The flow rate was 1 mL/min and the temperature was 40° C. The detection of the anthocyanidin compounds was carried out using a Shimazu SPD-M6A three dimensional detector at 400–650 nm.

The anthocyanidin peaks were identified by reference to known standards, viz: delphinidin, cyanidin and malvidin.

TLC analysis of anthocyanidins

Acid-hydrolysed pigment extracts were run in the Forestal solvent system (HOAc:water HCl; 30:10:3) (Markham, 1982). HPLC analysis of anthocyanins The delphinidin-3-glucoside peaks from the non-hydrolysed petal extracts of the SD petunia and an antisense aE10.9 transformant in VR were identified by HPLC with reference to a delphinidin-3-glucoside standard. The delphinidin-3-glucoside fractions were then purified twice by HPLC using gradient elution conditions of firstly 10% D to 60% D over 40 minutes then 60% D for 40 minutes. Collection of fractions was carried out at 39 to 46 minutes. The re-purification conditions were 20% D to 40% D over 40 minutes then 40% D for 30 minutes. Collections were taken at 38 to 45 minutes. (Solvent C was $H_2O$ and solvent D was 50% (v/v) acetonitrile, 0.5% (v/v) TFA). The purified fractions were then subjected to mass spectroscopy to confirm the identification of the compound as delphinidin-3-glucoside.

TLC analysis of antiocyanins

Aliquots of non-hydrolysed pigment extracts were spotted onto TLC plastic-coated cellulose plates (MERCK) and run in two separate solvent systems, 15% HOAc and BAW (Butan-1-ol:HOAc:water, 4:2:5).

EXAMPLE 15

COMPLEMENTATION OF A rt MUTANT (PCGP810 in SD)

The hybrid petunia line SD is homozygous recessive for the Rt gene. It produces pink flowers which accumulate delphinidin-3-glucoside pigments. A sense version of the aE10.9 cDNA was cloned behind the constitutive Mac promoter and introduced into SD. Three out of four independent transformants produced deeper coloured flowers. Thin layer chromatography (TLC) analysis of acid-hydrolysed extracts of these flowers revealed that malvidin was the major pigment produced in the petals. Since SD is dominant for Gf, Mt and Mf, the Rt mutation is the only lesion which prevents this line from producing malvidin (see FIG. 1B). Hence, the production of this pigment in the transgenic flowers provided compelling evidence that the aE10.9 cDNA can complement the Rt mutation and thus encodes 3Rt.

EXAMPLE 16

ANTISENSE SUPPRESSION OF 3RT ACTIVITY (PCGP811 in VR)

The aE10.9 cDNA was cloned behind the constitutive Mac promoter in an antisense orientation and introduced into the purple flowered VR petunia hybrid line. Seven out of 12 independent transformants showed an altered flower colour. In most-cases the flowers were a uniform shade of pink, but in two cases the flowers were variegated and contained purple and red sectors. HPLC and TLC analyses of non-hydrolysed petal extracts revealed that delphinidin-3-glucoside was the major pigment in the more lightly coloured transgenic flowers. Malvidin production was significantly reduced but not totally suppressed in all of the transgenic plants examined and there was increased production of petunidin (Table 7). Table 7, overleaf, shows the HPLC analysis of the anthocyanidins present in some of the flowers of the transgenic VR petunia plants transformed with pCGP811.

TABLE 7

| ACCESSION NUMBER | Genotype | Delphinidin ratio (%) RT = 7.5 m | Petunidin ratio (%) RT = 9.8 m | Malvidin ratio (%) RT = 13.5 m |
| --- | --- | --- | --- | --- |
| VR | Rt | — | 11.8% | 88.1% |
| 2125 | A/S Rt | 59.9% | 33.6% | 6.4% |
| 2129 | A/S Rt | 66.8% | 29.2% | 4.0% |
| 2131 | A/S Rt | 22.7% | 19.4% | 57.8% |
| Da | rt/rt | 94.9% | 3.8% | 1.3% |

A/S = antisense
RT = retention time
% ratio = % of anthocyanins detected

Figure 1A:
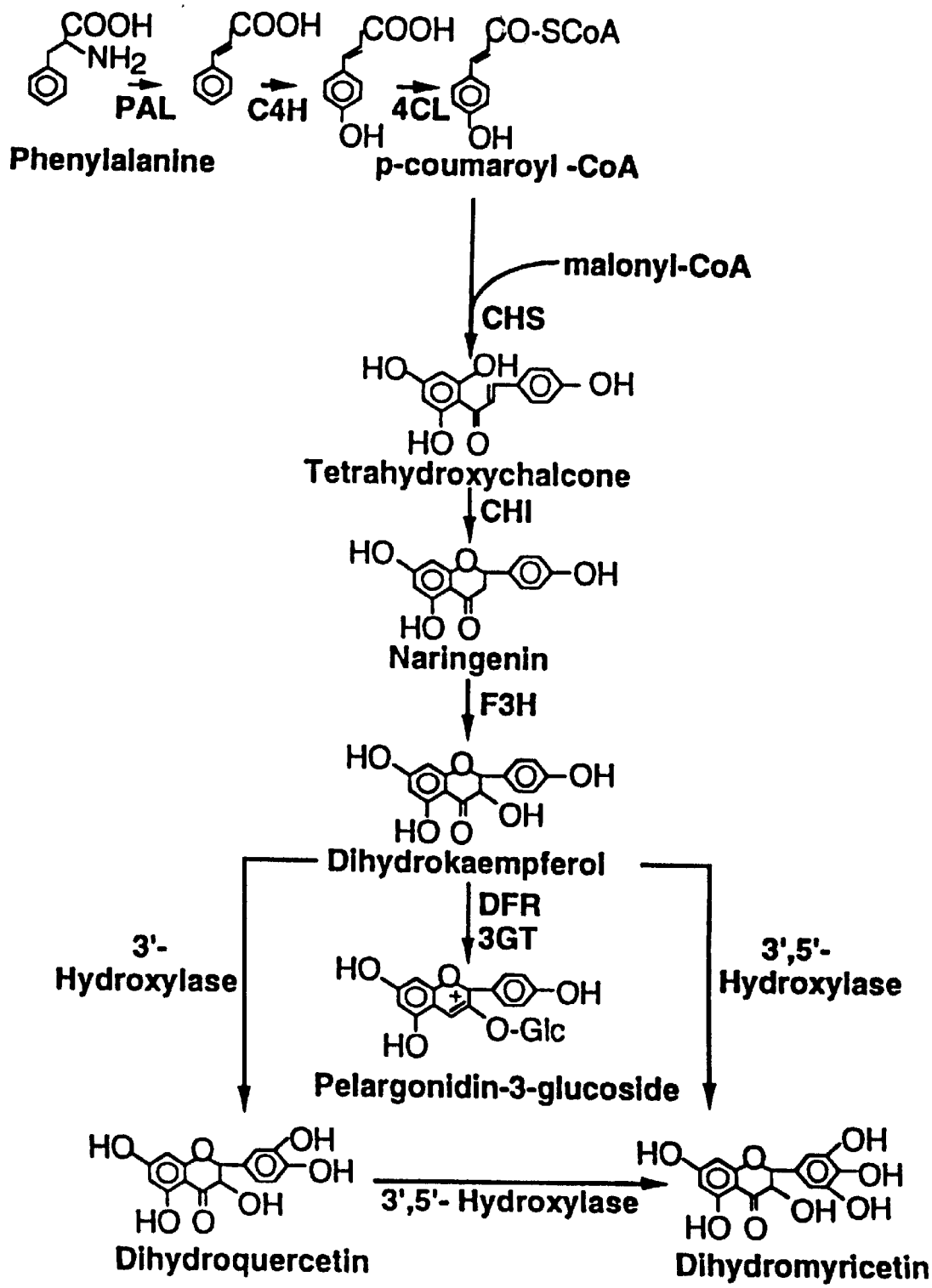
Figure 1B:
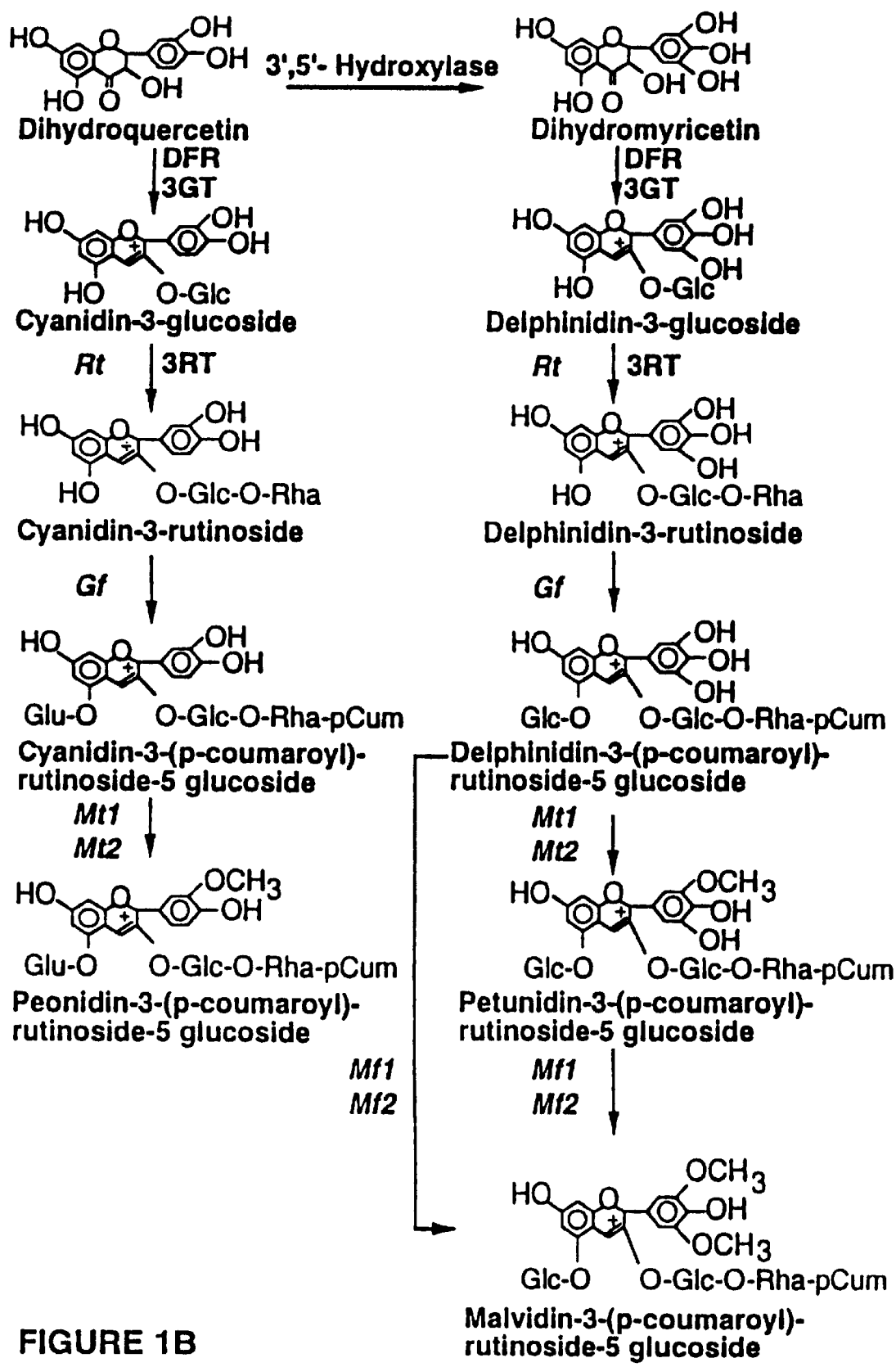

Antisense expression of the aE10.9 cDNA in VR plants interfered with the production of malvidin and resulted in accumulation of delphinidin-3-glucosides. This result supports the contention that the Rt locus encodes 3RT since rhamnosylation of anthocyanidin-3-glucosides precedes 5-O-glucosylation, acylation and methylation (FIG. 1). Interestingly, none of the transgenic plants had a pigment profile that exactly matched any previously characterized Rt mutant as in all cases there was some production of both petunidin and malvidin pigments. Presumably there was incomplete blockage of Rt gene activity. There was, however, a correlation between flower colour and the percentage of malvidin pigments present in petal extracts. The lighter coloured flowers contained lower amounts of malvidin than the darker coloured flowers. The transgenic flowers also contained higher levels of petunidin pigments compared to the VR control. Previous mutational studies would predict that any petunidin pigments formed should have been converted into malvidin pigments by the methyltransferases controlled by the Mf1 and Mf2 loci (Wiering and de Vlaming, 1984). However, Jonsson et al., (1984a & b) have reported that the amount of malvidin formed, relative to petunidin, varies with the substrate (delphinidin (3-p coumaroyl) rutinoside-5 glucoside) concentration and that high concentrations of the substrate inhibits the formation of malvidin. One possible explanation for these results is that high levels of delphinidin-3-glucosides may have some effect on the methylation reactions controlled by the M1 and Mf2 loci. Alternatively, a minimum concentration of petunidin substrate may be required for efficient 5' methylation.

EXAMPLE 17

TEMPORAL AND SPATIAL EXPRESSION OF Rt

The expression profile of the Rt gene was examined by RNA blot and in situ hybridization analysis.

Isolation of previously characterized flavonoid biosynthesis genes (a) CHI

A cDNA clone of chi-A (van Tunen et al., 1988) was synthesized by PCR using 10 ng from cDNA library #1 and two oligonucleotides, #2 (SEQ ID NO:6), which covered nucleotides 6–20 and #3, (SEQ ID NO:7) which was complementary to nucleotides 711–725 of the published chi-A cDNA sequence (van Tunen et al., 1988). The resulting PCR product was kinased and then ligated into the SmaI site of pBluescribe M13⁻ (Stratagene) and sequenced to confirm that the cloned fragment corresponded to the published sequence.

(b) DFR-A

The cDNA clone corresponding to dfr-A was isolated from the differential screen of cDNA library #1 and was identified by sequence analysis and comparison to the published sequence (Beld et al., 1989).

(c) PAL (i) Construction of cDNA library #3

Total RNA was isolated from stage 1 to 3 of $P.$ $hybrida$ cv OGB. Poly(A)⁺ RNA was purified by oligo-dT cellulose chromatography. Double-stranded cDNA was synthesized from 2.5 μg poly (A)⁺ RNA using a modification of the method of Lapeyre and Amalric (1985). The $S_1$ nuclease treatment of double-stranded cDNA prior to linker ligation was not performed. EcoRI-adaptors (Promega) ligated onto the double-stranded cDNA, the ligase was heat-killed (70° C. for 20 minutes) and the adaptors were kinased to allow subsequent ligation to the dephosphorylated vector DNA. Unligated adaptors and small cDNA molecules were removed by Sephadex S200 (Pharmacia) spun column chromatography. One quarter of the cDNA was ligated with 1 μg EcoRI-cut dephosphorylated lZAP (Stratagene). After packaging, the library was titred by transfecting $E.$ $coli$ BB4 and plating on NZY media containing X-gal. The library contained 23,000 recombinants.

(ii) Screening of cDNA library #3

The cDNA library #3 was screened with a PAL cDNA fragment from potato (a gift from Dr Imre E. Somssich, Max Planck Institute, Köln, Germany). Prehybridization (42° C., 1 hour) and hybridization (42° C., 16 hours) were carried out in 20% (v/v) formamide, 6×SSC and 1% (w/v) SDS. Low stringency wash conditions included 2×5 minutes in 2×SSC/ 0.1% (w/v) SDS at room temperature followed by 2×minutes in 2×SSC/0.1% (w/v) SDS at 42° C. The identification of the petunia PAL cDNA clone confirmed by sequence analysis and comparison to the published sequence from $Phaseolis$ $vulgaris$ (Edwards et al., 1985).

(d) CHS cDNA clone

An 8 kb petunia chs-A genomic fragment from pgP32 (Relf et al., 1985) was used to screen the cDNA library #1. A full length petunia chs-A cDNA clone was isolated using the standard hybridization condition previously described. The identification was confirmed by sequence analysis and comparison to the published sequence (Koes et al., 1986)

Glucose/high light induction of delphinidin synthesis in leaves

Leaves were harvested from $P.$ $hybrids$ cv OGB and cut into 1 cm² sections in sterile water. The leaf sections were then floated on a 2% (w/v) glucose solution and exposed to a light intensity of 24,000 lux for 96 hours.

Temporal expression

Developmental regulation

Total RNA from $P.$ $hybrida$ cv OGB petals harvested from flowers at the different stages of development defined in Example 1 above was examined for expression of various genes involved in the flavonoid biosynthetic pathway.

Figure 8:
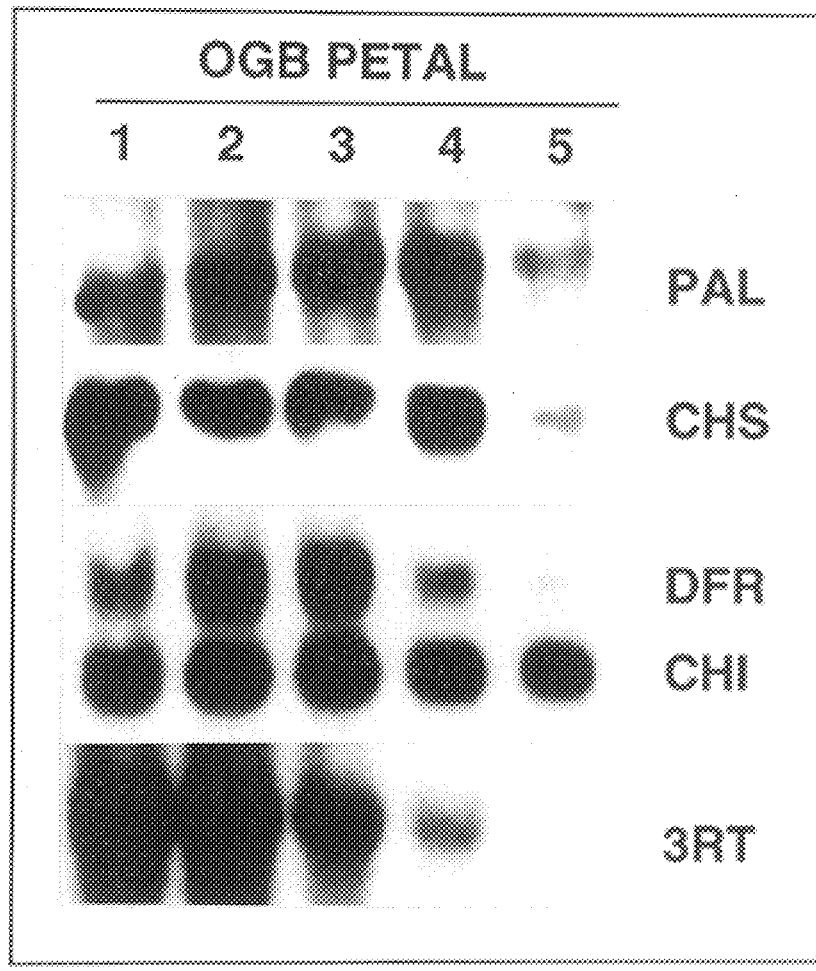
FIG. 8 is a RNA blot analysis showing the expression profiles of transcripts for PAL, CHS, CHI, DFR and 3RT. Hybridization with $^{32}$P-labelled probes to 20 μg of total RNA isolated from petals from the five developmental stages of P. hybrida cv OGB (1–5) described in Example 1.

The gene corresponding to the aE10.9 cDNA clone was found to be developmentally regulated during maturation of the corolla and generally peaked around stages 1–2 of flower development (FIG. 8). This developmental profile was similar to the expression of other genes involved in flavonoid biosynthesis although expression of CHS, CHI, DFR and PAL generally peaked at around stages 2–3 of flower development (FIG. 8).

(b) Induction of the anthocyanin pathway in leaf tissue

Figure 9:
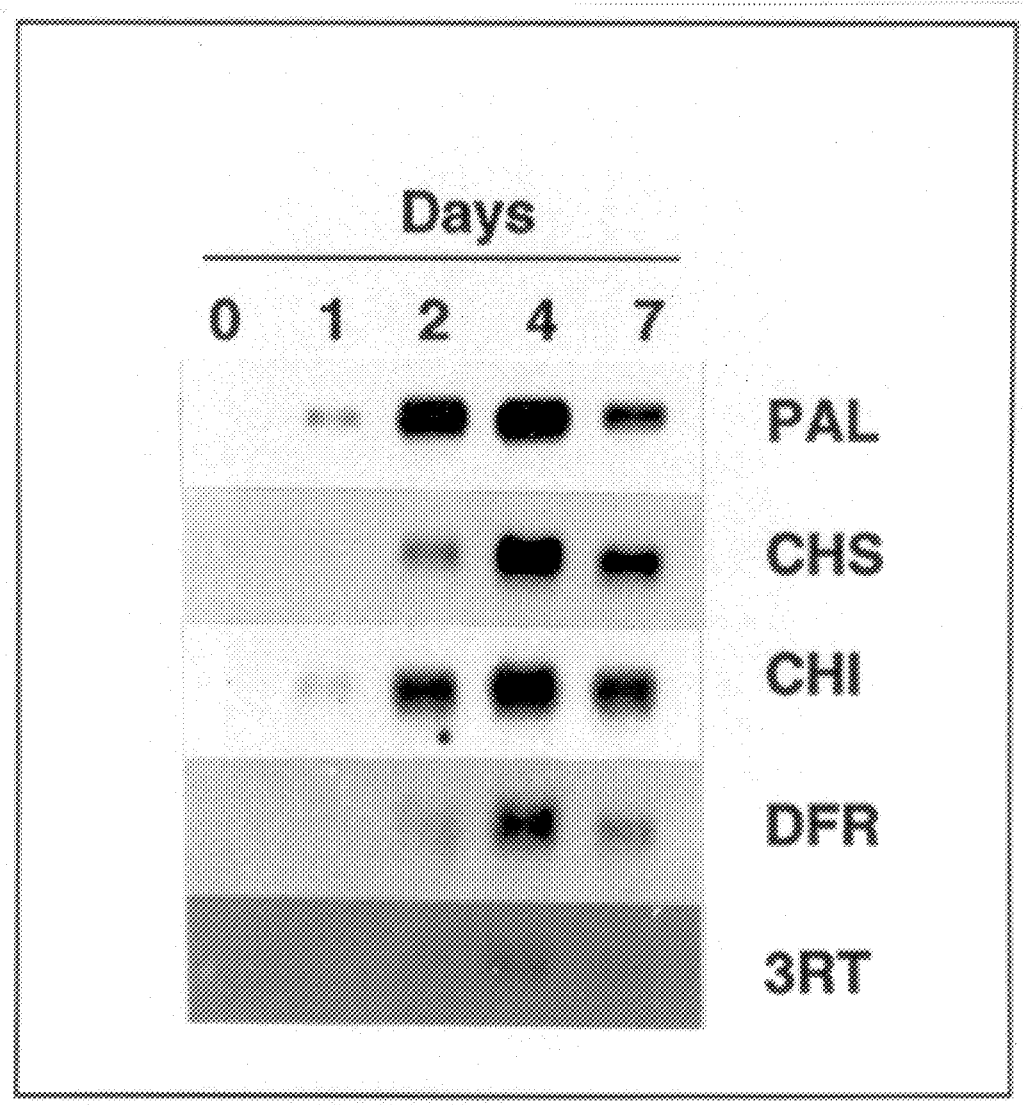
FIG. 9 is a RNA blot analysis showing the expression profiles of transcripts for PAL, CHS, CHI, DFR and 3RT. Hybridization with $^{32}$P-labelled probes to 20 μg of total RNA isolated from the five leaf tissue from 6 week old seedlings that had been incubated in 2% (w/v) glucose and exposed to high light for 0–7 days.

Genes of the flavonoid pigment biosynthetic pathway are not normally expressed in leaf tissue. However, synthesis of delphinidin pigments was induced in OGB leaves by incubation in a 2% (w/v) glucose solution in high light. Under these conditions, the gene corresponding to the aE10.9 cDNA clone was detected in OGB leaf tissue. Maximal induction of messenger RNA was shown to occur after 96 hours. The expression of several other biosynthesis genes was also induced (FIG. 9).

(c) Expression in different organs

Total RNA from various organs of $P.$ $hybrida$ cv OGB was examined for expression of the gene corresponding to the aE10.9 clone (FIG. 10). Message was detected in the petal and the stigma, although the latter was at a greatly reduced level. Therefore, the expression of the 3RT mRNA seems to be both developmentally-regulated in the petal and floral specific.

Spatial expression-In situ hybrdizations (a) Plant tissue preparation

Pedals were cut into 2–3 mm pieces and along with whole anthers and stigmas were fixed in 4% (v/v) paraformaldehyde in phosphate buffered saline (PBS) and 5 mM $MgCl_2$ pH7.4 for approximately 16–24 hours (Lawrence and Singer, 1985; Singer et al., 1986). Tissues were then dehydrated through a graded ethanol series and embedded in paraplast (Berlyn and Miksche, 1976). Transverse sections 10 μm thick were cut and mounted onto subbed slides. (Slides that had been treated with 2% 3-aminopropyltriethoxysilane in acetone for 5 minutes and then washed in distilled water and air dried).

(b) Preparation of RNA probes

Strand specific RNA probes were prepared using the Riboprobe reaction kit (Stratagene).

(c) Hybridization

Slides with mounted sections were deparaffinized in xylene and then hydrated by passage through a graded ethanol series as described by Martineau and Taylor (1986). The sections were then treated in PBS and 5 mM $MgCl_2$ for approximately 30 minutes, followed by 10 minutes in 0.1M Glycine, 0.2M Tris-HCl pH7.5.

For each slide, 1.2×10⁶ cpm of the RNA probe, 50 μg $E.$ $coli$ tRNA (Boehringer Mannheim) and 25 μg degraded herring sperm DNA (Sigma) were lyophilized and then resuspended in 25 μL deionized formamide (BDH) that had been heated to 90° C. A 25 μL aliquot of 2×hybridization mix was then added to give a final concentration of 2×SSC, 0.2% (w/v) BSA, 10% (w/v) dextran sulphate, 75 mM DTT, 1 unit/μL of RNasin ribonuclease inhibitor (Promega) and 50% (v/v) formamide. A 40 μL droplet was placed on the section and coverslipped. The hybridizations were carried out in a humidified chamber at 37° C. for 16 hours.

Washing was carried out in 50% (v/v) formamide, 2×SSC, 20 mM DTT for 5 minutes at room temperature to remove the coverslips followed by 30 minutes, at 42° C. in 10 μg/mL RNase A, 500 mM NaCl, 10 mM Tris-HCl pH 8.0, 20 mM DTT then 2×SSC, 20 mM DTT and 1×SSC, 20 mM DTT. The final wash was in 1×SSC, 20 mM DTT at room temperature for a further 30 minutes. The slides were then dehydrated in a graded ethanol series as described by Martineau and Taylor (1986). The slides were air dried and then exposed to Fuji RX film at −70° C. for 16 hours to gauge the length of exposure to the nuclear track emulsion (Coghlan et al., 1985). The slides were then coated in Kodak NTB-2 liquid nuclear track emulsion (diluted 1:1 with distilled water) at 45° C., allowed to drain in a vertical position and then placed in a light tight box with silica gel crystals (6–18 mesh) (BDH) and stored at 4° C. for 5 days. Slides were developed as described in Martineau and Taylor (1986). The slides were washed in running water for 15 minutes and then dehydrated through a graded ethanol series followed by passage through xylene: 95% ethanol (1:1) and xylene. The slides were then permanently mounted with Euckitt (O. Kindler).

Slides were examined under a Nikon photomicroscope. The control slide was one hybridized with the sense transcript as an indication of background. Photographs were taken with Kodak Ektachrome 160T film.

The spatial expression of the Rt transcript was examined by in situ hybridization. On petal sections the aE10.9 cDNA bound predominantly to the epidermal cells although limited hybridization to mesophyll cells was detected (FIG. 11). This corresponded to anthocyanin pigment accumulation which is essentially localized to the epidermal layers of the petal. Preliminary in situ hybridization experiments on style and anther sections have also detected a Rt transcript in these organs.

As part of a program to isolate cDNA clones involved in the anthocyanin pathway a differential screening approach was used to screen an OGB petal cDNA library with cDNA probes prepared from OGB petals (limb and tube) of stages 3–4 flowers and R51 petals (tube). The petunia line R51 is mutant in several loci known to be involved in anthocyanin biosynthesis and also carries a blind mutation which leads to the formation of flowers consisting mostly of tubes with reduced limbs. Two classes of cDNA clones would be detected by this differential screen, those that were preferentially expressed in limb as compared to tube tissue and those that were down-regulated due to specific mutations. The cDNA clone aE10.9 showed sequence similarities to previously sequenced glycosyltransferases. RFLP and RNA blot analyses provided strong evidence that this cDNA corresponds to the Rt locus which is homozygous recessive in R51. This was verified by complementation between a Rt mutation and the aE10.9 cDNA. Furthermore, antisense expression of the aE10.9 cDNA clone inhibited rhamnosylation of the anthocyanidin-3-glucosides.

Those skilled in the art, however, will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Alexander, D. C., McKnight, T. D. and Williams, B. G., *Gene* 31: 79–89, 1984.

Allday, M. J. and Jones, M. D., *Nucleic Acids Research* 15(24):10592, 1987.

Andersen, O. M., *Biochem, Syst. Ecol.*, 16(6): 535–540, 1988.

Asen, S., *J. Am, Soc. Hortic. Sci.* 107(5): 744–750, 1982.

Asen, S. and Griesbach, R., *J. Am. Soc. Hortic. Sci.* 108(5): 845–850, 1983.

Asen, S., Griesbach, R. J., Norris, K. H. and Leonhardt, B. A., *Phytochemistry*, 25(11): 2509–2514, 1986.

Aviv, H. and Leder, P., *Proc. Natl. Acad. Sci. USA* 69: 1408, 1972.

Beld, M., Martin, C., Huits, H., Stuitje, A. R. and Gerats, A. G. M., *Plant Molecular Biology* 13: 491–502, 1989.

Berlyn, G. P. and Miksche, J. P., Botanical microtechnique and cytochemistry. Iowa State Uni Press, Ames, Iowa, 1976.

Bethesda Research Laboratories. BRL pUC host: *E. coli* DH5a™ competent cells. *Bethesda Res. Lab. Focus.* 8(2): 9, 1986.

Budzianowski, J., *Phytochemistry* 30(5): 1679–1682, 1991.

Bullock, W. O., Fernandez. J. M. and Short, J. M., *Biotechniques* 5: 376, 1987.

Coghlan, J. P., Aldred, P., Haralambidis, J., Niall, H. D., Penschow, J. D. and Tregear, G. W., *Analytical Biochemistry* 149: 1–28, 1985.

Comai, L., Moran, P. and Maslyar, D., *Plant Molecular Biology* 15: 373–381, 1990.

Cornu, A., *Mutation Research,* 42: 235–248, 1977.

Cornu, A., Farcy, E., Maizonnier, D., Haring, M., Veerman, W. and Gerats, A. G. M., In: *Genetic maps—Locus maps of complex genomes.* 5th edition, Stephen J. O'Brien (ed.), Cold Spring Harbor Laboratory Press, U.S.A., 1990.

Dellaporta, S. J., Wood, J. and Hick, J. B., *Plant Mol. Biol. Rep.* 1: 19–21, 1983.

Doodeman, M., Gerats, A. G. M., Schram, A. W., De Vlaming, P. and Bianchi, F., *Theor. Appl. Genet.* 67: 357–366, 1984.

Ebel, J. and Hahlbrock. K., In: *The Flavonoids: Advances in Research Since* 1980. Harbourne, J. B. (ed.), Academic Press. New York, U.S.A., 641–679, 1988.

Edwards, K., Cramer, C. L., Bolwell, G. P., Dixon, R. A., Schuch, W. and Lamb, C. J., *Proc. Natl. Acad. Sci. USA* 82: 6731–6735, 1985.

Furtek, D., Schiefelbein, J. W., Johnston, F. and Nelson, O. E., *Plant Mol. Biol.* 11: 473–481, 1988.

Gamborg, O. L., Miller, R. A. and Ojima, K., *Exp. Cell Res.* 50: 151–158, 1968.

Garfinkel, D. J. and Nester, E. W., *J.Bact.* 144: 732–743, 1980.

Gerats, A. G. M., Farcy, E., Wallroth, M., Groot, S. P. C. and Schram, A. *Generics,* 106: 501–508, 1984.

Gerats, A. G. M., Hiuts, H., Vrijlandt, E., Marana, C., Souer, E. and Beld, M., *The Plant Cell* 2: 1121–1128, 1990.

Gerats, A. G. M., de Vlaming, P., Doodeman, M., Al, B. and Schram, A. W., *Planta* 155: 364–368, 1982.

Hahlbrock. K. and Grisebach, H., *Annu. Rev. Plant Physiol.* 30: 105–130, 1979.

Hanahan, D., *J. Mol. Biol.* 166: 557, 1983.

Harborne, J. B. and Nash, R. J., *Biochem. Syst. Ecol.* 12(3): 315–318, 1984.

Harborne, J. B. and Williams, C. A. Z *Naturforsch* 39(1–2): 18–23, 1984.

Haseloff, J. and Gerlach, L. *Nature* 334: 586–591, 1988.

Higgins, D. G. and Sharp, P. M., *Gene* 73: 237–244, 1988.

Holton, T. A. and Graham, M. W., *Nucleic Acids Research* 19:1156, 1991.

Inoue, H., Nojima, H. and Okayama, H., *Gene* 96: 23–28, 1990.

Itokawa, H., Oshida. Y., Ikuta. A., Inatomi, H. and Ikegami, S., *Phytochemistry* 20(10): 2421–2422, 1981.

Jefferson, R. A., Kavanagh, T. A. and Bevan, M. W., *EMBO J.* 6(13): 3901–3907, 1987.

Jonsson, L. M. V., Aarsman, M. E. G., Schram, A. W. and Bennink, G. J. H., *Phytochemistry* 21(10): 2457–2460, 1982.

Jonsson, L. M. V., Aarsman, M. E. G., de Vlaming, P. and Schram, A. W., *Theor. Appl. Genet.* 68: 459–466, 1984a.

Jonsson, L. M. V., Aarsman, M. E. G., Poulton, J. E. and Schram, A. W. *Planta* 160: 174–179, 1984b.

Jonsson, L. M. V., Aarsman. M. E. G., van Diepen, P., Smit, N. and Schram, A. W., *Planta* 160: 341–347, 1984c.

Kamsteeg, J., van Brederode, J. and van Nigtevecht, G., *Z. Naturforsch* 35c: 249–257, 1979.

Kimura, T. and Owens, I. S., *Eur J Biochem* 168: 515–521, 1987.

Joshi, C. P., *Nucleic Acids Research* 15: 9627–9640, 1987.

Khokhar, J. A., Humphreys, J. M., Short, K. C. and Grout, B. W. W., *Hortscience* 17(5): 810–811, 1982.

Koes, R. E., Spelt, C. E., Reif, H. J., van den Elzen. P. J. M., Veltkamp, E. and Mol, J. N. M., *Nucl Acids Res.* 14(13): 5229–5239, 1986.

Lapeyre. B. and Amalric, F., *Gene* 37: 215–220, 1985.

Lawrence, J. B. and Singer, R. H., *Nucleic Acids Research* 13(5): 1777–1799, 1985.

Lazo, G. R., Pascal, A. S. and Ludwig, R. A., Bio/technology 9: 963–967, 1991.

Mackenzie, P. I., *J Biol Chem* 261: 6119–6125, 1986.

Maizonnier, D. and Moessner, A., *Generica* 52(2): 143–148, 1980.

Maniatis, T., Fritsch, E. F. and Sambrook, J. *Molecular Cloning: A Laboratory Manual.*, Cold Spring Harbor Laboratory Press, U.S.A. 1982.

Markham, K. R., *Techniques of flavonoid identification.*, Academic Press, London, 1982.

Martin, C. Prescott, A., Mackay, S., Bartlett, J. and Vrijlandt, E., *The Plant Journal* 1(1): 37–49, 1991.

Martineau, B. and Taylor, W. C., *Plant Physiol* 82: 613–618, 1986.

McBride, K. E. and Summerfelt, K. R., *Plant Molecular Biology* 14: 269–276 1990.

Miyajima, I., Doi. I. and Kage, T., *Sci. Bull. Fac. Agric. Kyushu Univ.* 45(1–2): 83–90, 1990.

Murashige, T. and Skoog, F., *Physiol. Plant* 15: 73–97, 1962.

Nakano, K., Nishizawa, K., Takemoto, I., Murakami, K., Takaishi, Y. and Tomimatsu, T., *Phytochemistry* 28(1): 301–303, 1989.

O'Reilly, D. R. and Miller, L. K., *Science* 24:1110–1112, 1989.

O'Reilly, D. R. and Miller, L. K., *J Virol* 64: 1321–1328, 1990.

Pearson, W. R. and Lipman, D. J., *Proc. Natl Acad Sci. USA* 85: 2444–2448, 1988.

Ralston, E. J., English, J. J. and Dooner, H. K., *Genetics* 119: 185–197, 1988.

Reif, H. J., Niesbach, U., Deumling, B. and Saedler, H., *Mol. Gen, Gent.* 199: 208–215, 1985.

Ritter, J. K., Crawford, J. M. and Owens I. S., *J Biol Chem* 266: 1043–1047, 1991.

Saito, N. and Harborne, J. B., *Phytochemistry* 1735–1740, 1983.

Saito, N., Yokoi, M., Ogawa, M., Kamijo, M. and Honda, T., *Phytochemistry* 27(5): 1399–1402, 1988.

Sambrook, J., Fritsch, E. F. and Maniatis, T., *Molecular Cloning: A Laboratory Manual.* (2nd edition), Cold Spring Harbor Laboratory Press, U.S.A., 1989.

Sanger, F., Nicklen, S. and Coulson, A., *Proc. Natl. Acad Sci. USA* 74: 5463–5467, 1977.

Schenk, R. U. and Hilderbrandt, A. C., *Can. J. Bot.* 50: 199–204, 1972.

Schram, A. W., Jonsson, L. M. V. and Bennink, G. J. H., Biochemistry of flavonoid synthesis in Petunia hybrida. In: Petunia Sink, K. C. (ed.), Springer-Verlag, Berlin, Germany, pp 68–75, 1984.

Seitz, H. U. and Hinderer, W., Anthocyanins. In: *Cell Culture and Somatic Cell Generics of Plants.* Constabel, F. and Vasil, I. K. (eds.), Academic Press, New York, U.S.A., 5:49–76, 1988.

Singer, R. H., Lawrence, J. B. and Villnave, C., *Biotechniques* 4(3): 230–250, 1986.

Stafford, H. A., *Flavonoid Metabolism.* CRC Press, Inc. Boca Raton, Fla., U.S.A., 1990.

Snook, M. E., Chortyk, O. T., Sisson, V. A. and Costello, C. E., *Phytochemistry* 31(5): 1639–1647, 1992.

Turpen, T. H. and Griffith, O. M., *BioTechniques* 4: 11–15, 1986.

van Tunen, A. J., Koes, R. E., Spelt, C. E. van der Krol, A. R., Stuitje, A. R. and Mol. J. N. M., *EMBO J.,* 7(5): 1257–1263, 1988.

Vidal-Ollivier, E., Elias, R. Faure., F., Babadjamian, A., Crespim, F., Balansard, G. and Boudon, G., *Planta Medica* 55(1): 73–74, 1989.

Wallroth, M., Gerats, A. G. M., Rogers, S. G., Fraley, R. T. and Horsch, R. B., *Mol. Gen. Genet.* 202: 6–15, 1986.

Wiering, H. and De Vlaming, P., Inheritance and Biochemistry of Pigments. In: *Petunia* Sink, K. C. (ed.). Springer-Verlag, Berlin, Germany, pp 49–65, 1984.

Wise, R. P., Rohde, W. and Salamini, F., *Plant Mol Biol.* 14: 277–279, 1990.

Yadav, S. P. and Brew. K., *J Biol Chem* 266: 698–703, 1991.

We claim:

1. An isolated nucleic acid molecule comprising a sequence of nucleotides encoding, or complementary to, a sequence encoding a plant anthocyanidin-3-glucoside rhamnosyltransferase (3RT).

2. An isolated nucleic acid molecule according to claim 1 wherein the plant is selected from the group consisting of *Petunia hybrida, Silene diocia,* Antirrhinum, *cyclamen,* Alstroemeria, Metrosideros, Potentilla and Saintpaulia.

3. An isolated nucleic acid molecule according to claim 2 wherein the plant is *Petunia hybrida*.

4. An isolated nucleic acid molecule according to claim 3 comprising a nucleotide sequence, or complementary to a nucleotide sequence as set forth in SEQ ID NO:2 or having at least 50% similarity thereto.

5. An isolated DNA molecule comprising a sequence of nucleotides which
   (i) encodes a 3RT; and
   (ii) has at least 50% nucleotide sequence similarity to the sequence set forth in SEQ ID NO:2.

6. An isolated DNA molecule according to claim 5 further comprising the nucleotide sequence set forth in SEQ ID NO:3.

7. An isolated nucleic acid molecule which:
   (i) encodes a 3RT of plant origin; and
   (ii) hybridizes under low stringency conditions to the nucleotide sequence set forth in SEQ ID No:2 or to a complementary strand thereof.

8. An isolated nucleic acid molecule according to claim 7 further comprising the nucleotide sequence set forth in SEQ ID NO:3.

9. An isolated nucleic acid molecule according to any one of claims 4 to 8 wherein the 3RT is of petunia origin.

10. A vector comprising the nucleic acid molecule according to any one of claims 5 to 8.

11. A vector according to claim 10 wherein the nucleic acid molecule is operably linked to a promoter.

12. A vector according to claim 11 which is capable of replication and expression in a eukaryotic cell.

13. A vector according to claim 11 which is capable of replication and expression in a prokaryotic cell.

14. A transgenic plant comprising a nucleic acid molecule having a sequence of nucleotides encoding, or complementary to, a sequence encoding a plant 3RT.

15. A transgenic plant according to claim 14 wherein the expression is regulatable.

16. A transgenic plant according to claim 15 wherein the expression is developmentally regulated.

17. A transgenic plant according to claim 14 wherein the 3RT is of *Petunia hybrida, Silene dioica,* Antirrhinum, *cyclamen,* Alstromeria, Metrosideros, Potentilla or Saintpaulia origin.

18. A transgenic plant according to claim 17 wherein the glycosyltransferase is of *Petunia hybrida* origin.

19. A transgenic plant according to claim 18 wherein the 3RT comprises an amino acid sequence set forth in SEQ ID NO:2 or has at least 50% similarity thereto.

20. A transgenic plant according to claim 14 wherein said plant is selected from the group consisting of petunia, rose, carnation, chrysanthemum, gerbera, tobacco, lisianthus, lily, iris and pelargonium.

21. A transgenic plant selected from the group consisting of petunia, rose, carnation, chrysanthemum, gerbera, tobacco, lisianthus, lily, iris and pelargonium capable of regulated expression of a non-indigenous 3RT, wherein said 3RT encoded by a DNA molecule comprising a DNA strand capable of hybridizing under low stringency conditions to a nucleic acid molecule comprising the sequence of nucleotides set forth in SEQ ID NO:2.

22. A method for producing a transgenic flowering plant capable of exhibiting altered flower color, said method comprising introducing into a cell of a suitable plant, the nucleic acid molecule according to any one of claims 4 to 8, regenerating a transgenic plant from the cell and growing said transgenic plant for a time and under conditions sufficient to permit expression of the nucleic acid sequence into a 3RT.

23. A method according to claim 22 wherein the transgenic plant is selected from the list consisting of petunia, rose, carnation, chrysanthemum, gerbera, tobacco, lisianthus, lily, iris and pelargonium.

24. A method according to claim 23 wherein the introduced nucleic acid is DNA and encodes 3RT from *Petunia hybrida* having the nucleotide sequence as set forth in SEQ ID NO:2 or a nucleic acid encoding 3RT from *Petunia hybrida* comprising a deletion or substitution of at least one nucleotide set forth in SEQ ID No:2 and which codes for a protein which maintains 3RT activity.

25. A method according to claim 24 wherein the nucleotide sequence further comprises the sequence set forth in SEQ ID NO:3.

26. A method of producing a transgenic flowering plant capable of exhibiting altered flower color, which comprises introducing into a cell of a plant carrying an indigenous 3RT, the nucleic acid according to any one of claims 4 to 8 under conditions to induce co-suppression of said 3RT.

27. A method according to claim 26 wherein the transgenic plant is selected from the list consisting of petunia, rose, carnation, chrysanthemum, gerbera, tobacco, lisianthus, lily, iris and pelargonium.

28. A method according to claim 23 wherein the introduced nucleic acid is DNA and encodes 3RT from *Petunia hybrida* having the nucleotide sequence as set forth in at least one of SEQ ID NO:2 or SEQ ID NO:3 or a nucleic acid encoding 3RT from *Petunia hybrida* comprising a deletion or substitution of at least one nucleotide set forth in at least one of SEQ ID No:2 or SEQ ID No:3 and which codes for a protein which maintains 3RT activity.

29. A cut flower from the transgenic plant of claim 22.
30. A cut flower from the transgenic plant of claim 23.
31. A cut flower from the transgenic plant of claim 24.
32. A cut flower from the transgenic plant of claim 25.
33. A cut flower from the transgenic plant of claim 26.
34. A cut flower from the transgenic plant of claim 27.
35. A cut flower from the transgenic plant of claim 28.

* * * * *

UNITED STATES PATENT AND TRADEMARK OFFICE
CERTIFICATE OF CORRECTION

PATENT NO. : 5,859,334
DATED : January 12, 1999
INVENTOR(S) : F. Brugliera, et al.

It is certified that error appears in the above-identified patent and that said Letters Patent is hereby corrected as shown below:

Column 11, Line 24: "five" should read --OGB--

Column 11, Line 45: "1" should read --l--

Column 11, Line 50: "one" should read --the--

Column 17 and 18, TABLE 3A, Line 43: "ETACL" should read --ETSAL--

Column 19 & 20, TABLE 4, Line 33: "HaG" should read --HAG--

Column 22, Line 55: "5 µof" should read --5 µg of--

Column 23, Line 10: "(v/v)" should read --(w/v)--

Column 25, Line 43: "antiocyanins" should read --anthocyanins--

Column 27, Line 60: "1986)" should read --1986).--

Column 27, Line 64: "hybrids" should read --hybrida--

Column 28, Line 2: "Developmental" should read --(a) Developmental--

UNITED STATES PATENT AND TRADEMARK OFFICE
CERTIFICATE OF CORRECTION

PATENT NO. : 5,859,334
DATED : January 12, 1999
INVENTOR(S) : F. Bruglicra, et al.

It is certified that error appears in the above-identified patent and that said Letters Patent is hereby corrected as shown below:

Column 30, Line 1: "Am," should read --Am.--

Column 32, Line 9: "1735-1740" should read --22(8): 1735-1740--

Signed and Sealed this

Twenty-ninth Day of May, 2001

Attest:

NICHOLAS P. GODICI

Attesting Officer     *Acting Director of the United States Patent and Trademark Office*

UNITED STATES PATENT AND TRADEMARK OFFICE
CERTIFICATE OF CORRECTION

PATENT NO. : 5,859,334
DATED : January 12, 1999
INVENTOR(S) : Filippa Brugliera et al.

It is certified that error appears in the above-identified patent and that said Letters Patent is hereby corrected as shown below:

Column 17,
Line 43, Table 3A, "ETACL" should read -- ETSCL --

Signed and Sealed this

Twenty-fifth Day of May, 2004

JON W. DUDAS
*Acting Director of the United States Patent and Trademark Office*